US011877825B2

(12) United States Patent
Siepser et al.

(10) Patent No.: US 11,877,825 B2
(45) Date of Patent: Jan. 23, 2024

(54) DEVICE ENUMERATION IN AN OPTICAL MEASUREMENT SYSTEM

(71) Applicant: HI LLC, Los Angeles, CA (US)

(72) Inventors: Benjamin Siepser, Los Angeles, CA (US); Sangyong Park, Castro Valley, CA (US); Sebastian Sorgenfrei, Playa Vista, CA (US); Jacob Dahle, Arlington, MA (US); Ryan Field, Culver City, CA (US); Alex Borisevich, Los Angeles, CA (US); Milin J. Patel, Anaheim, CA (US)

(73) Assignee: HI LLC, Los Angeles, CA (US)

( * ) Notice: Subject to any disclaimer, the term of this patent is extended or adjusted under 35 U.S.C. 154(b) by 485 days.

(21) Appl. No.: 17/202,548

(22) Filed: Mar. 16, 2021

(65) Prior Publication Data

US 2021/0290065 A1   Sep. 23, 2021

Related U.S. Application Data

(60) Provisional application No. 63/051,093, filed on Jul. 13, 2020, provisional application No. 62/992,485, filed on Mar. 20, 2020.

(51) Int. Cl.
  *A61B 5/00*   (2006.01)
  *G01J 1/42*   (2006.01)
  *G01J 1/44*   (2006.01)
(52) U.S. Cl.
  CPC .......... *A61B 5/0075* (2013.01); *G01J 1/4228* (2013.01); *G01J 1/44* (2013.01); *A61B 5/0042* (2013.01);
  (Continued)
(58) Field of Classification Search
  CPC .................................................... G06F 16/955
  See application file for complete search history.

(56) References Cited

U.S. PATENT DOCUMENTS

| 4,018,534 A | 4/1977 | Thorn et al. |
| 4,207,892 A | 6/1980 | Binder |

(Continued)

FOREIGN PATENT DOCUMENTS

| CN | 200950235 | 9/2007 |
| CN | 107865635 | 4/2018 |

(Continued)

OTHER PUBLICATIONS

Alayed, et al., "Characterization of a Time-Resolved Diffuse Optical Spectroscopy Prototype Using Low-Cost, Compact Single Photon Avalanche Detectors for Tissue Optics Applications," Sensors 2018, 18, 3680; doi:10.3390/s18113680, Oct. 29, 2018.

(Continued)

*Primary Examiner* — Henry Tsai
*Assistant Examiner* — Juanito C Borromeo
(74) *Attorney, Agent, or Firm* — ALG Intellectual Property, LLC

(57) ABSTRACT

An exemplary system includes a processor, a wearable device comprising a plurality of slots, and a first module including a plurality of detectors and a module control circuit. The processor is configured to successively transmit, to each slot of the plurality of slots, a command to enable a respective module located in each slot. The processor is further configured to determine, based on an acknowledgment received from the module control circuit, that the first module is enabled and located in a first slot, and to successively transmit, based on the determining that the first module is enabled and located in the first slot, a plurality of detector address identifiers. The module control circuit is configured to successively place the plurality of detectors into an enumeration mode in which each detector of the plurality of detectors is assigned a different detector address identifier of the plurality of detector address identifiers.

29 Claims, 16 Drawing Sheets

(52) U.S. Cl.
CPC . *A61B 2562/0238* (2013.01); *G01J 2001/442* (2013.01); *G01J 2001/448* (2013.01); *G01J 2001/4466* (2013.01)

(56) References Cited

U.S. PATENT DOCUMENTS

| | | | |
|---|---|---|---|
| 4,281,645 A | 8/1981 | Jobsis | |
| 4,321,930 A | 3/1982 | Jobsis | |
| 4,515,165 A | 5/1985 | Carroll | |
| 4,655,225 A | 4/1987 | Dahne et al. | |
| 4,928,248 A | 5/1990 | Takahashi et al. | |
| 4,963,727 A | 10/1990 | Cova | |
| 4,995,044 A | 2/1991 | Blazo | |
| 5,088,493 A | 2/1992 | Giannini | |
| 5,090,415 A | 2/1992 | Yamashita | |
| 5,309,458 A | 5/1994 | Carl | |
| 5,386,827 A | 2/1995 | Chance et al. | |
| 5,528,365 A | 6/1996 | Gonatas et al. | |
| 5,625,458 A | 4/1997 | Alfano et al. | |
| 5,761,230 A | 6/1998 | Oono et al. | |
| 5,853,370 A | 12/1998 | Chance et al. | |
| 5,895,984 A | 4/1999 | Renz | |
| 5,929,982 A | 7/1999 | Anderson | |
| 5,983,120 A | 11/1999 | Groner et al. | |
| 5,987,045 A | 11/1999 | Albares et al. | |
| 6,163,715 A | 12/2000 | Larsen et al. | |
| 6,240,309 B1 | 5/2001 | Yamashita et al. | |
| 6,291,824 B1 | 9/2001 | Battarbee et al. | |
| 6,384,663 B2 | 5/2002 | Cova et al. | |
| 6,541,752 B2 | 4/2003 | Zappa et al. | |
| 6,618,614 B1 | 9/2003 | Chance | |
| 6,640,133 B2 | 10/2003 | Yamashita | |
| 6,683,294 B1 | 1/2004 | Herbert et al. | |
| 6,748,254 B2 | 6/2004 | O'Neil | |
| 6,992,772 B2 | 1/2006 | Block | |
| 7,095,491 B2 | 8/2006 | Forstner et al. | |
| 7,356,365 B2 | 4/2008 | Schurman | |
| 7,507,596 B2 | 3/2009 | Yaung et al. | |
| 7,547,872 B2 | 6/2009 | Niclass et al. | |
| 7,613,504 B2 | 11/2009 | Rowe | |
| 7,667,400 B1 | 2/2010 | Goushcha | |
| 7,705,284 B2 | 4/2010 | Inoue et al. | |
| 7,714,292 B2 | 5/2010 | Agarwal et al. | |
| 7,774,047 B2 | 8/2010 | Yamashita et al. | |
| 7,899,506 B2 | 3/2011 | Xu et al. | |
| 8,026,471 B2 | 9/2011 | Itzler | |
| 8,078,250 B2 | 12/2011 | Chen et al. | |
| 8,082,015 B2 | 12/2011 | Yodh et al. | |
| 8,115,170 B2 | 2/2012 | Stellari et al. | |
| 8,168,934 B2 | 5/2012 | Niclass et al. | |
| 8,352,012 B2 | 1/2013 | Besio | |
| 8,633,431 B2 | 1/2014 | Kim | |
| 8,637,875 B2 | 1/2014 | Finkelstein et al. | |
| 8,754,378 B2 | 6/2014 | Prescher et al. | |
| 8,817,257 B2 | 8/2014 | Herve | |
| 8,937,509 B2 | 1/2015 | Xu et al. | |
| 8,986,207 B2 | 3/2015 | Li | |
| 9,012,860 B2 | 4/2015 | Nyman et al. | |
| 9,041,136 B2 | 5/2015 | Chia | |
| 9,058,081 B2 | 6/2015 | Baxter | |
| 9,076,707 B2 | 7/2015 | Harmon | |
| 9,101,279 B2 | 8/2015 | Ritchey et al. | |
| 9,131,861 B2 | 9/2015 | Ince et al. | |
| 9,157,858 B2 | 10/2015 | Claps | |
| 9,160,949 B2 | 10/2015 | Zhang et al. | |
| 9,176,241 B2 | 11/2015 | Frach | |
| 9,178,100 B2 | 11/2015 | Webster et al. | |
| 9,190,552 B2 | 11/2015 | Brunel et al. | |
| 9,201,138 B2 | 12/2015 | Eisele et al. | |
| 9,209,320 B1 | 12/2015 | Webster | |
| 9,257,523 B2 | 2/2016 | Schneider et al. | |
| 9,257,589 B2 | 2/2016 | Niclass et al. | |
| 9,299,732 B2 | 3/2016 | Webster et al. | |
| 9,299,873 B2 | 3/2016 | Mazzillo et al. | |
| 9,312,401 B2 | 4/2016 | Webster | |
| 9,316,735 B2 | 4/2016 | Baxter | |
| 9,331,116 B2 | 5/2016 | Webster | |
| 9,368,487 B1 | 6/2016 | Su et al. | |
| 9,401,448 B2 | 7/2016 | Bienfang et al. | |
| 9,407,796 B2 | 8/2016 | Dinten et al. | |
| 9,419,635 B2 | 8/2016 | Kumar et al. | |
| 9,431,439 B2 | 8/2016 | Soga et al. | |
| 9,442,201 B2 | 9/2016 | Schmand et al. | |
| 9,449,377 B2 | 9/2016 | Sarkar et al. | |
| 9,450,007 B1 | 9/2016 | Motta et al. | |
| 9,466,631 B2 | 10/2016 | Fallica et al. | |
| 9,476,979 B2 | 10/2016 | Drader et al. | |
| 9,478,579 B2 | 10/2016 | Dai et al. | |
| 9,529,079 B1 | 12/2016 | Droz | |
| 9,535,157 B2 | 1/2017 | Caley et al. | |
| 9,574,936 B2 | 2/2017 | Heinonen | |
| 9,625,580 B2 | 4/2017 | Kotelnikov et al. | |
| 9,627,569 B2 | 4/2017 | Harmon | |
| 9,634,826 B1 | 4/2017 | Park | |
| 9,639,063 B2 | 5/2017 | Dutton et al. | |
| 9,640,704 B2 | 5/2017 | Frey et al. | |
| 9,658,158 B2 | 5/2017 | Renna et al. | |
| 9,659,980 B2 | 5/2017 | Mcgarvey et al. | |
| 9,671,284 B1 | 6/2017 | Dandin | |
| 9,681,844 B2 | 6/2017 | Xu et al. | |
| 9,685,576 B2 | 6/2017 | Webster | |
| 9,702,758 B2 | 7/2017 | Nouri | |
| 9,728,659 B2 | 8/2017 | Hirigoyen et al. | |
| 9,741,879 B2 | 8/2017 | Frey et al. | |
| 9,753,351 B2 | 9/2017 | Eldada | |
| 9,767,246 B2 | 9/2017 | Dolinsky et al. | |
| 9,768,211 B2 | 9/2017 | Harmon | |
| 9,773,930 B2 | 9/2017 | Motta et al. | |
| 9,804,092 B2 | 10/2017 | Zeng et al. | |
| 9,812,438 B2 | 11/2017 | Schneider et al. | |
| 9,831,283 B2 | 11/2017 | Shepard et al. | |
| 9,851,302 B2 | 12/2017 | Mattioli Della Rocca et al. | |
| 9,867,250 B1 | 1/2018 | Powers et al. | |
| 9,869,753 B2 | 1/2018 | Eldada | |
| 9,881,963 B1 | 1/2018 | Chen et al. | |
| 9,882,003 B1 | 1/2018 | Aharoni | |
| 9,886,095 B2 | 2/2018 | Pothier | |
| 9,899,544 B1 | 2/2018 | Mazzillo et al. | |
| 9,899,557 B2 | 2/2018 | Muscara' et al. | |
| 9,939,316 B2 | 4/2018 | Scott et al. | |
| 9,939,536 B2 | 4/2018 | O'Neill et al. | |
| 9,946,344 B2 | 4/2018 | Ayaz et al. | |
| D817,553 S | 5/2018 | Aaskov et al. | |
| 9,983,670 B2 | 5/2018 | Coleman | |
| 9,997,551 B2 | 6/2018 | Mandai et al. | |
| 10,016,137 B1 | 7/2018 | Yang et al. | |
| D825,112 S | 8/2018 | Saez | |
| 10,056,415 B2 | 8/2018 | Na et al. | |
| 10,103,513 B1 | 10/2018 | Zhang et al. | |
| 10,141,458 B2 | 11/2018 | Zhang et al. | |
| 10,157,954 B2 | 12/2018 | Na et al. | |
| 10,158,038 B1 | 12/2018 | Do Valle et al. | |
| 10,219,700 B1 | 3/2019 | Yang et al. | |
| 10,256,264 B2 | 4/2019 | Na et al. | |
| 10,340,408 B1 | 7/2019 | Katnani | |
| 10,424,683 B1 | 9/2019 | Do Valle | |
| 10,483,125 B2 | 11/2019 | Noue | |
| 10,515,993 B2 | 12/2019 | Field et al. | |
| 10,533,893 B2 | 1/2020 | Leonardo | |
| 10,541,660 B2 | 1/2020 | McKisson | |
| 10,558,171 B2 | 2/2020 | Kondo | |
| 10,594,306 B2 | 3/2020 | Dandin | |
| 10,627,460 B2 | 4/2020 | Alford et al. | |
| 10,695,167 B2 | 6/2020 | Van Heugten et al. | |
| 10,697,829 B2 | 6/2020 | Delic | |
| 10,772,561 B2 | 9/2020 | Donaldson | |
| 10,809,796 B2 | 10/2020 | Armstrong-Muntner | |
| 10,825,847 B2 | 11/2020 | Furukawa | |
| 10,912,504 B2 | 2/2021 | Nakaji | |
| 10,976,386 B2 | 4/2021 | Alford | |
| 10,983,177 B2 | 4/2021 | JiméNez-MartÍNez | |
| 10,996,293 B2 | 5/2021 | Mohseni | |
| 11,006,876 B2 | 5/2021 | Johnson | |
| 11,006,878 B2 | 5/2021 | Johnson | |

(56) References Cited

U.S. PATENT DOCUMENTS

| | | |
|---|---|---|
| 11,137,283 B2 | 10/2021 | Balamurugan et al. |
| 11,630,310 B2 | 4/2023 | Seidman et al. |
| 2002/0195545 A1 | 12/2002 | Nishimura |
| 2004/0057478 A1 | 3/2004 | Saito |
| 2004/0078216 A1 | 4/2004 | Toto |
| 2004/0160996 A1 | 8/2004 | Giorgi et al. |
| 2005/0038344 A1 | 2/2005 | Chance |
| 2005/0061986 A1 | 3/2005 | Kardynal et al. |
| 2005/0124863 A1 | 6/2005 | Cook |
| 2005/0228291 A1 | 10/2005 | Chance |
| 2006/0171845 A1 | 8/2006 | Martin |
| 2006/0197452 A1 | 9/2006 | Zhang |
| 2006/0264722 A1 | 11/2006 | Hannula et al. |
| 2007/0038116 A1 | 2/2007 | Yamanaka |
| 2007/0083097 A1 | 4/2007 | Fujiwara |
| 2008/0021341 A1 | 1/2008 | Harris et al. |
| 2009/0012402 A1 | 1/2009 | Mintz |
| 2009/0054789 A1 | 2/2009 | Kiguchi et al. |
| 2009/0163775 A1 | 6/2009 | Barrett |
| 2009/0313048 A1 | 12/2009 | Kahn et al. |
| 2010/0188649 A1 | 7/2010 | Prahl et al. |
| 2010/0210952 A1 | 8/2010 | Taira et al. |
| 2010/0249557 A1 | 9/2010 | Besko et al. |
| 2010/0301194 A1 | 12/2010 | Patel |
| 2011/0208675 A1 | 8/2011 | Shoureshi et al. |
| 2011/0248175 A1 | 10/2011 | Frach |
| 2012/0016635 A1 | 1/2012 | Brodsky et al. |
| 2012/0029304 A1 | 2/2012 | Medina et al. |
| 2012/0083673 A1 | 4/2012 | Al-Ali et al. |
| 2012/0101838 A1 | 4/2012 | Lingard et al. |
| 2013/0015331 A1 | 1/2013 | Birk |
| 2013/0030267 A1 | 1/2013 | Lisogurski |
| 2013/0030270 A1 | 1/2013 | Chiou et al. |
| 2013/0032713 A1 | 2/2013 | Barbi et al. |
| 2013/0090541 A1 | 4/2013 | Macfarlane et al. |
| 2013/0144644 A1 | 6/2013 | Simpson |
| 2013/0221221 A1 | 8/2013 | Bouzid et al. |
| 2013/0225953 A1 | 8/2013 | Oliviero et al. |
| 2013/0342835 A1 | 12/2013 | Blacksberg |
| 2014/0027607 A1 | 1/2014 | Mordarski et al. |
| 2014/0028211 A1 | 1/2014 | Imam |
| 2014/0055181 A1 | 2/2014 | Chavpas |
| 2014/0066783 A1 | 3/2014 | Kiani |
| 2014/0171757 A1 | 6/2014 | Kawato et al. |
| 2014/0185643 A1 | 7/2014 | McComb et al. |
| 2014/0191115 A1 | 7/2014 | Webster et al. |
| 2014/0211194 A1 | 7/2014 | Pacala et al. |
| 2014/0217264 A1 | 8/2014 | Shepard |
| 2014/0275891 A1 | 9/2014 | Muehlemann et al. |
| 2014/0289001 A1 | 9/2014 | Shelton |
| 2014/0291481 A1 | 10/2014 | Zhang et al. |
| 2015/0038811 A1 | 2/2015 | Asaka |
| 2015/0038812 A1 | 2/2015 | Ayaz et al. |
| 2015/0041625 A1 | 2/2015 | Dutton |
| 2015/0041627 A1 | 2/2015 | Webster |
| 2015/0054111 A1 | 2/2015 | Niclass et al. |
| 2015/0057511 A1 | 2/2015 | Basu |
| 2015/0077279 A1 | 3/2015 | Song |
| 2015/0094552 A1 | 4/2015 | Golda |
| 2015/0150505 A1 | 6/2015 | Kaskoun et al. |
| 2015/0157262 A1 | 6/2015 | Schuessler |
| 2015/0157435 A1 | 6/2015 | Chasins et al. |
| 2015/0182136 A1 | 7/2015 | Durduran et al. |
| 2015/0192677 A1 | 7/2015 | Yu et al. |
| 2015/0200222 A1 | 7/2015 | Webster |
| 2015/0201841 A1 | 7/2015 | Ishikawa et al. |
| 2015/0293224 A1 | 10/2015 | Eldada et al. |
| 2015/0327777 A1 | 11/2015 | Kostic et al. |
| 2015/0333095 A1 | 11/2015 | Fallica et al. |
| 2015/0364635 A1 | 12/2015 | Bodlovic et al. |
| 2016/0049765 A1 | 2/2016 | Eldada |
| 2016/0099371 A1 | 4/2016 | Webster |
| 2016/0119983 A1 | 4/2016 | Moore |
| 2016/0150963 A1 | 6/2016 | Roukes et al. |
| 2016/0161600 A1 | 6/2016 | Eldada et al. |
| 2016/0181302 A1 | 6/2016 | Mcgarvey et al. |
| 2016/0182902 A1 | 6/2016 | Guo |
| 2016/0218236 A1 | 7/2016 | Dhulla et al. |
| 2016/0247301 A1 | 8/2016 | Fang |
| 2016/0278715 A1 | 9/2016 | Yu et al. |
| 2016/0287107 A1 | 10/2016 | Szabados |
| 2016/0296168 A1 | 10/2016 | Abreu |
| 2016/0341656 A1 | 11/2016 | Liu et al. |
| 2016/0345880 A1 | 12/2016 | Nakaji et al. |
| 2016/0356718 A1 | 12/2016 | Yoon et al. |
| 2016/0357260 A1 | 12/2016 | Raynor et al. |
| 2017/0030769 A1 | 2/2017 | Clemens et al. |
| 2017/0047372 A1 | 2/2017 | Mcgarvey et al. |
| 2017/0052065 A1 | 2/2017 | Sharma et al. |
| 2017/0085547 A1 | 3/2017 | De Aguiar et al. |
| 2017/0118423 A1 | 4/2017 | Zhou et al. |
| 2017/0124713 A1 | 5/2017 | Jurgenson et al. |
| 2017/0131143 A1 | 5/2017 | Andreou et al. |
| 2017/0139041 A1 | 5/2017 | Drader et al. |
| 2017/0141100 A1 | 5/2017 | Tseng et al. |
| 2017/0164857 A1 | 6/2017 | Brugere |
| 2017/0176579 A1 | 6/2017 | Niclass et al. |
| 2017/0176596 A1 | 6/2017 | Shpunt et al. |
| 2017/0179173 A1 | 6/2017 | Mandai et al. |
| 2017/0186798 A1 | 6/2017 | Yang et al. |
| 2017/0202518 A1 | 7/2017 | Furman et al. |
| 2017/0265822 A1 | 9/2017 | Du |
| 2017/0276545 A1 | 9/2017 | Henriksson |
| 2017/0281086 A1 | 10/2017 | Donaldson |
| 2017/0299700 A1 | 10/2017 | Pacala et al. |
| 2017/0303789 A1 | 10/2017 | Tichauer et al. |
| 2017/0314989 A1 | 11/2017 | Mazzillo et al. |
| 2017/0363467 A1 | 12/2017 | Clemens et al. |
| 2017/0367650 A1 | 12/2017 | Wallois |
| 2018/0003821 A1 | 1/2018 | Imai |
| 2018/0014741 A1 | 1/2018 | Chou |
| 2018/0019268 A1 | 1/2018 | Zhang et al. |
| 2018/0020960 A1 | 1/2018 | Sarussi |
| 2018/0026147 A1 | 1/2018 | Zhang et al. |
| 2018/0027196 A1 | 1/2018 | Yang et al. |
| 2018/0033895 A1 | 2/2018 | Mazzillo et al. |
| 2018/0039053 A1 | 2/2018 | Kremer et al. |
| 2018/0045816 A1 | 2/2018 | Jarosinski et al. |
| 2018/0062345 A1 | 3/2018 | Bills et al. |
| 2018/0066986 A1 | 3/2018 | Kasai et al. |
| 2018/0069043 A1 | 3/2018 | Pan et al. |
| 2018/0070830 A1 | 3/2018 | Sutin et al. |
| 2018/0070831 A1 | 3/2018 | Sutin et al. |
| 2018/0081061 A1 | 3/2018 | Mandai et al. |
| 2018/0089531 A1 | 3/2018 | Geva et al. |
| 2018/0089848 A1 | 3/2018 | Yang et al. |
| 2018/0090526 A1 | 3/2018 | Mandal et al. |
| 2018/0090536 A1 | 3/2018 | Mandai et al. |
| 2018/0102442 A1 | 4/2018 | Wang et al. |
| 2018/0103528 A1 | 4/2018 | Moore |
| 2018/0103861 A1 | 4/2018 | Sutin et al. |
| 2018/0117331 A1 | 5/2018 | Kuzniecky |
| 2018/0120152 A1 | 5/2018 | Leonardo |
| 2018/0122560 A1 | 5/2018 | Okuda |
| 2018/0156660 A1 | 6/2018 | Turgeon |
| 2018/0167606 A1 | 6/2018 | Cazaux et al. |
| 2018/0175230 A1 | 6/2018 | Droz et al. |
| 2018/0180473 A1 | 6/2018 | Clemens et al. |
| 2018/0185667 A1 | 7/2018 | Huang |
| 2018/0217261 A1 | 8/2018 | Wang |
| 2018/0296094 A1 | 10/2018 | Nakamura |
| 2018/0366342 A1 | 12/2018 | Inque et al. |
| 2019/0006399 A1 | 1/2019 | Otake et al. |
| 2019/0025406 A1 | 1/2019 | Krelboim et al. |
| 2019/0026849 A1 | 1/2019 | Demeyer |
| 2019/0088697 A1 | 3/2019 | Furukawa et al. |
| 2019/0091483 A1 | 3/2019 | Deckert |
| 2019/0113385 A1 | 4/2019 | Fukuchi |
| 2019/0120975 A1 | 4/2019 | Ouvrier-Buffet |
| 2019/0167211 A1 | 6/2019 | Everman et al. |
| 2019/0175068 A1 | 6/2019 | Everdell |
| 2019/0192031 A1 | 6/2019 | Laszlo et al. |
| 2019/0200888 A1 | 7/2019 | Poltorak |
| 2019/0209012 A1 | 7/2019 | Yoshimoto et al. |

(56) References Cited

U.S. PATENT DOCUMENTS

| | | |
|---|---|---|
| 2019/0261869 A1 | 8/2019 | Franceschini |
| 2019/0298158 A1 | 10/2019 | Dhaliwal |
| 2019/0343395 A1 | 11/2019 | Cussac |
| 2019/0355773 A1 | 11/2019 | Field et al. |
| 2019/0355861 A1 | 11/2019 | Katnani |
| 2019/0363210 A1 | 11/2019 | Do Valle |
| 2019/0378869 A1 | 12/2019 | Field et al. |
| 2019/0388018 A1 | 12/2019 | Horstmeyer |
| 2019/0391213 A1 | 12/2019 | Alford |
| 2020/0022581 A1 | 1/2020 | Vanegas |
| 2020/0041727 A1 | 2/2020 | Yamamoto |
| 2020/0044098 A1 | 2/2020 | Azuma |
| 2020/0056263 A1 | 2/2020 | Bhattacharyya |
| 2020/0057115 A1 | 2/2020 | Jiménez-Martínez |
| 2020/0057116 A1 | 2/2020 | Zorzos et al. |
| 2020/0060542 A1 | 2/2020 | Alford |
| 2020/0088811 A1 | 3/2020 | Mohseni |
| 2020/0109481 A1 | 4/2020 | Sobek |
| 2020/0123416 A1 | 4/2020 | Bhattacharyya |
| 2020/0136632 A1 | 4/2020 | Lin |
| 2020/0182692 A1 | 6/2020 | Lilic |
| 2020/0188030 A1 | 6/2020 | Kopper et al. |
| 2020/0191883 A1 | 6/2020 | Bhattacharyya |
| 2020/0196932 A1 | 6/2020 | Johnson |
| 2020/0241094 A1 | 7/2020 | Alford |
| 2020/0253479 A1 | 8/2020 | Nurmikko |
| 2020/0256929 A1 | 8/2020 | Ledbetter et al. |
| 2020/0309873 A1 | 10/2020 | Ledbetter et al. |
| 2020/0315510 A1 | 10/2020 | Johnson |
| 2020/0334559 A1 | 10/2020 | Anderson |
| 2020/0337624 A1 | 10/2020 | Johnson |
| 2020/0341081 A1 | 10/2020 | Mohseni et al. |
| 2020/0348368 A1 | 11/2020 | Garber et al. |
| 2020/0381128 A1 | 12/2020 | Pratt |
| 2020/0390358 A1 | 12/2020 | Johnson |
| 2020/0393902 A1 | 12/2020 | Mann et al. |
| 2020/0400763 A1 | 12/2020 | Pratt |
| 2021/0015385 A1 | 1/2021 | Katnani |
| 2021/0011094 A1 | 2/2021 | Bednarke |
| 2021/0041512 A1 | 2/2021 | Pratt |
| 2021/0063510 A1 | 3/2021 | Ledbetter |
| 2021/0013974 A1 | 5/2021 | Seidman |
| 2021/0139742 A1 | 5/2021 | Seidman |
| 2021/0265512 A1 | 8/2021 | Ayel |
| 2021/0290064 A1 | 9/2021 | Do Valle |
| 2021/0294996 A1 | 9/2021 | Field |

FOREIGN PATENT DOCUMENTS

| | | |
|---|---|---|
| EP | 0656536 | 4/2004 |
| EP | 2294973 | 3/2011 |
| EP | 3419168 | 12/2018 |
| EP | 3487072 | 5/2019 |
| KR | 20170087639 A | 7/2017 |
| WO | 8804034 | 6/1988 |
| WO | 1999053577 | 10/1999 |
| WO | 2008144831 | 12/2008 |
| WO | 2011083563 | 7/2011 |
| WO | 2012135068 | 10/2012 |
| WO | 2013034770 | 3/2013 |
| WO | 2013066959 | 5/2013 |
| WO | 2015052523 | 4/2015 |
| WO | 2015109005 | 7/2015 |
| WO | 2016166002 | 10/2016 |
| WO | 2017004663 | 1/2017 |
| WO | 2017083826 | 5/2017 |
| WO | 2017130682 | 8/2017 |
| WO | 2017150146 | 9/2017 |
| WO | 2017203936 | 11/2017 |
| WO | 2018007829 | 1/2018 |
| WO | 2018033751 | 2/2018 |
| WO | 2018122560 | 7/2018 |
| WO | 2019221784 | 11/2019 |

OTHER PUBLICATIONS

Bellis, et al., "Photon counting imaging: the DigitalAPD," Society of Photo-Optical Instrumentation Engineers (SPIE) Conference Series, Feb. 2006, vol. 6068, pp. 111-120.

Blutman, et al., "A 0.1 pJ Freeze Vernier Time-to-Digital Converter in 65nm CMOS," 2014 International Symposium on Circuits and Systems (ISCAS), Melbourne, Australia, Jun. 1-5, 2014.

Cambie, et al.,"Every photon counts: understanding and optimizing photon paths in luminescent solar concentrator-based photomicroreactors (LSC-PMs)," React. Chem. Eng., 2017, 2, 561-566.

Contini, et al., "Photon migration through a turbid slab described by a model based on diffusion approximation. I. Theory," Appl. Opt. 36(19), 4587 (1997).

Dalla Mora, et al., "Fast-Gated Single-Photon Avalanche Diode for Wide Dynamic Range Near Infrared Spectroscopy," IEEE Journal of Selected Topics in Quantum Electronics, vol. 16, No. 4, Jul./Aug. 2010.

Dalla Mora, et al., "Memory effect in silicon time-gated single-photon avalanche diodes," http://dx.doi.org/10.1063/1.4915332, Journal of Applied Physics 117, 114501, 2015.

De Heyn, et al., "A fast start-up 3GHz-10GHz digitally controlled oscillator for UWB impulse radio in 90nm CMOS," 2007 European Solid-State Circuits Conference—(ESSCIRC), Munich, Germany, pp. 484-487 Sep. 11-13, 2007.

Di Sieno, et al., "Probe-hosted large area silicon photomultiplier and high-throughput timing electronics for enhanced performance time-domain functional near-infrared spectroscopy," Biomed. Opt. Express 11(11), 6389 (2020).

Dutton, et al., "A Time-Correlated Single-Photon-Counting Sensor with 14GS/s Histogramming Time-to-Digital Converter," 2015 IEEE International Solid-State Circuits Conference ISSCC 2015 / SESSION 11 / Sensors and Imagers for Life Sciences / 11.5, Feb. 22-26, 2015.

Fishburn, et al., "Temporal Derivative Distribution Repair (TDDR): A motion correction method for fNIRS," Neuroimage. Jan. 1, 2019; 184: 171-179. doi:10.1016/j.neuroimage.2018.09.025.

Fisher, et al., "A Reconfigurable Single-Photon-Counting Integrating Receiver for Optical Communications," IEEE Journal of Solid-State Circuits, vol. 48, No. 7, Jul. 2013, https://www.researchgate.net/publication/260626902.

Gallivanoni, et al., "Progress in Quenching Circuits for Single Photon Avalanche Diodes," IEEE Transactions on Nuclear Science, vol. 57, No. 6, Dec. 2010.

Gnecchi, et al., "A 1×16 SiPM Array for Automotive 3D Imaging LiDAR Systems.", *Proceedings of the 2017 International Image Sensor Workshop (IISW), Hiroshima, Japan*, (2017).

Harmon, et al., "Compound Semiconductor SPAD Arrays," LightSpin Technologies, http://www.lightspintech.com/publications.html (2013).

Henderson, et al.,"A 192 × 128 Time Correlated SPAD Image Sensor in 40-nm CMOS Technology," IEEE Journal of Solid-State Circuits, 2019.

Henderson, et al., "A 256×256 40nm/90nm CMOS 3D-Stacked 120dB Dynamic-Range Reconfigurable Time-Resolved SPAD Imager," 2019 IEEE International Solid-State Circuits Conference—(ISSCC), San Francisco, CA, USA, 2019, pp. 106-108. doi: 10.1109/ISSCC.2019.8662355.

Huppert, et al., "HomER: a review of time-series analysis methods for near-infrared spectroscopy of the brain," Appl. Opt. 48(10), D280 (2009).

Kienle, et al.,"Improved solutions of the steady-state and the time-resolved diffusion equations for reflectance from a semi-infinite turbid medium," J. Opt. Soc. Am. A 14(1), 246 (1997).

Konugolu, et al., "Broadband (600-1350 nm) Time-Resolved Diffuse Optical Spectrometer for Clinical Use," IEEE Journal of Selected Topics in Quantum Electronics, vol. 22, No. 3, May/Jun. 2016.

Lacerenza, et al., "Wearable and wireless time-domain near-infrared spectroscopy system for brain and muscle hemodynamic monitoring," Biomed. Opt. Express 11(10), 5934 (2020).

(56) References Cited

OTHER PUBLICATIONS

Lange, et al.,"Clinical Brain Monitoring with Time Domain NIRS: A Review and Future Perspectives," Applied Sciences 9(8), 1612 (2019).
Lange, et al., "MAESTROS: A Multiwavelength Time-Domain NIRS System to Monitor Changes in Oxygenation and Oxidation State of Cytochrome-C-Oxidase," IEEE J. Select. Topics Quantum Electron. 25(1), 1-12 (2019).
Lee, et al., "High-Performance Back-Illuminated Three-Dimensional Stacked Single-Photon Avalanche Diode Implemented in 45-nm CMOS Technology," IEEE Journal of Selected Topics in Quantum Electronics 6, 1-9 (2018).
Mandai, et al.,"A 4 × 4 × 416 digital SiPM array with 192 TDCs for multiple high-resolution timestamp acquisition," 2013 JINST 8 P05024, May 31, 2013.
Martelli, et al., "Optimal estimation reconstruction of the optical properties of a two-layered tissue phantom from time-resolved single-distance measurements," Journal of Biomedical Optics 20(11), 115001 (Nov. 2015).
Maruyama, et al., "A 1024 × 8, 700-ps Time-Gated SPAD Line Sensor for Planetary Surface Exploration With Laser Raman Spectroscopy and LIBS," IEEE Journal of Solid-State Circuits, vol. 49, No. 1, Jan. 2014.
Mita, et al., "High-Speed and Compact Quenching Circuit for Single-Photon Avalanche Diodes," IEEE Transactions on Instrumentation and Measurement, vol. 57, No. 3, Mar. 2008. pp. 543-547.
Mora, et al., "Fast silicon photomultiplier improves signal harvesting and reduces complexity in time-domain diffuse optics," Opt. Express 23(11), 13937 (2015).
Mora, et al., "Fast-Gated Single-Photon Avalanche Diode for Wide Dynamic Range Near Infrared Spectroscopy," IEEE Journal of Selected Topics in Quantum Electronics, vol. 16, No. 4, pp. 1023-1030, Jul./Aug. 2010.
Parmesan, et al., "A 256 ×256 SPAD array with in-pixel Time to Amplitude Conversion for Fluorescence Lifetime Imaging Microscopy," *Memory 900.M4*, 2015.
Pifferi, et al., "Performance assessment of photon migration instruments: the MEDPHOT protocol," Applied Optics, 44(11), 2104-2114 (2005).
Prahl, et al., "Optical Absorption of Hemoglobin," http://omic.ogi.edu/spectra/hemoglobin/index.html (1999).
Puszka, et al.,"Time-resolved diffuse optical tomography using fast-gated single-photon avalanche diodes," Biomedical optics express, 2013, vol. 4, No. 8, pp. 1351-1365 (Year: 2013).
Re, et al.,"Multi-channel medical device for time domain functional near infrared spectroscopy based on wavelength space multiplexing," Biomed. Opt. Express 4(10), 2231 (2013).
Renna, et al.,"Eight-Wavelength, Dual Detection Channel Instrument for Near-Infrared Time-Resolved Diffuse Optical Spectroscopy," IEEE J. Select. Topics Quantum Electron. 25(1), 1-11 (2019).
Richardson, et al.,"A 32x×32 50ps resolution 10 bit time to digital converter array in 130nm CMOS for time correlated imaging," CICC 2009 Proceedings of the IEEE 2009 Custom Integrated Circuits Conference. IEEE Society, San Jose, U.S.A., pp. 77-80, CICC 2009, San Jose, U.S.A., Sep. 13, 2009. https://doi.org/doi:10.1109/CICC.2009.5280890.
Takai, et al., "Single-Photon Avalanche Diode with Enhanced NIR-Sensitivity for Automotive LIDAR Systems," Sensors, 2016, 16(4): 459, pp. 1-9 (Year: 2016).
Torricelli, et al., "Time domain functional NIRS imaging for human brain mapping," NeuroImage 85, 28-50 (2014).
Wabnitz, et al., "Depth-selective data analysis for time-domain fNIRS: moments vs. time windows," Biomed. Opt. Express 11(8), 4224 (2020).
Wabnitz, et al., "Performance assessment of time-domain optical brain imagers, part 1: basic instrumental performance protocol," Journal of Biomedical Optics 19(8), 086010 (Aug. 2014).
Wabnitz, et al., "Performance assessment of time-domain optical brain imagers, part 2: nEUROPt protocol," Journal of Biomedical Optics 19(8), 086012 (Aug. 2014).
Wojtkiewicz, et al., "Self-calibrating time-resolved near infrared spectroscopy," Biomed. Opt. Express 10(5), 2657 (2019).
Zhang, et al.,"A CMOS SPAD Imager with Collision Detection and 128 Dynamically Reallocating TDCs for Single-Photon Counting and 3D Time-of-Flight Imaging," Sensors (Basel, Switzerland), 18(11), 4016. doi:10.3390/s18114016 Nov. 17, 2018.
Zucchelli, et al., "Method for the discrimination of superficial and deep absorption variations by time domain fNIRS," 2013 OSA Dec. 1, 2013 | vol. 4, No. 12 | DOI:10.1364/BOE.4.002893 | Biomedical Optics Express 2893.
"emojipedia.org", https://emojipedia.org (accessed May 27, 2021).
"International Search Report and Written Opinion received in International Application No. PCT/2021/018188".
"International Search Report and Written Opinion received in International Application No. PCT/US2021/018155".
"International Search Report and Written Opinion received in International Application No. PCT/US2021/018187".
"International Search Report and Written Opinion received in International Application No. PCT/US2021/018190".
"scienceofpeople.com/emojis", https://www.scienceofpeople.com/emojis/ (accessed May 27, 2021).
Hebert, et al., "Spatiotemporal image correlation spectroscopy (STICS) theory, verification, and application to protein velocity mapping in living CHO cells", Biophysical journal 88, No. 5 (2005): 3601-3614.
Kheng, et al., "Image Processing", https://www.comp.nus.edu.sg/~cs4243/lecture/imageproc.pdf, Mar. 9, 2014.
Sneha, et al., "Understanding Correlation", https://www.allaboutcircuits.com/technical-articles/understanding-correlation/, Jan. 4, 2017.
Xu, et al.,"A 655 µW Silicon Photomultiplier-Based NIRS/EEG/EIT Monitoring ASIC for Wearable Functional Brain Imaging", IEEE Transactions on Biomedical Circuits and Systems, IEEE, US, vol. 12, No. 6, Dec. 1, 2018.
Zucconi, et al.,"The Autocorrelation Function", https://www.alanzucconi.com/2016/06/06/autocorrelation-function/, Jun. 6, 2016.
Chen, et al., "A PVT Insensitive Field Programmable Gate Array Time-to-digital Converter", 2013 IEEE Nordic-Mediterranean Workshop on Time-To-Digital Converters. Oct. 3, 2013.
Field, et al., "A 100-fps, Time-Correlated Single-PhotonCounting-Based Fluorescence-Lifetime Imager in 130-nm CMOS", IEEE Journal of Solid-State Circuits, vol. 49, No. 4, Apr. 2014.
Lebid, et al., "Multi-Timescale Measurements of Brain Responses in Visual Cortex During Functional Stimulation Using Time-Resolved Spectroscopy", SPIE vol. 5826. Dec. 31, 2005. p. 609, last paragraph—p. 610, paragraph 1.
Zheng, et al., "An Integrated Bias Voltage Control Method for SPAD Arrays", Oct. 1, 2018, IEEE Service Center.
International Search Report and Written Opinion received in International Application No. PCT/2020/027537, dated Sep. 7, 2020.
International Search Report and Written Opinion received in International Application No. PCT/2020/028820, dated Aug. 26, 2020.
International Search Report and Written Opinion received in International Application No. PCT/US20/34062, dated Aug. 26, 2020.
International Search Report and Written Opinion received in International Application No. PCT/US2018/058580, dated Feb. 12, 2019.
International Search Report and Written Opinion received in International Application No. PCT/US2018/062777, dated Feb. 13, 2019.
International Search Report and Written Opinion received in International Application No. PCT/US2019/019317, dated May 28, 2019.
Non-Final Office Action received in U.S. Appl. No. 16/177,351, dated Apr. 1, 2019.
Non-Final Office Action received in U.S. Appl. No. 16/283,730, dated May 16, 2019.
Non-Final Office Action received in U.S. Appl. No. 16/370,991, dated Feb. 10, 2020.
Non-Final Office Action received in U.S. Appl. No. 16/537,360, dated Feb. 25, 2020.

(56) References Cited

OTHER PUBLICATIONS

Non-Final Office Action received in U.S. Appl. No. 16/544,850, dated Jun. 25, 2020.
Non-Final Office Action received in U.S. Appl. No. 16/856,524, dated Dec. 1, 2020.
Partial Search Report received in International Application No. PCT/2020/028820, dated Jul. 1, 2020.
Partial Search Report received in International Application No. PCT/US2020/027537, dated Jul. 17, 2020.

DEVICE ENUMERATION IN AN OPTICAL MEASUREMENT SYSTEM

RELATED APPLICATIONS

The present application claims priority under 35 U.S.C. § 119(e) to U.S. Provisional Patent Application No. 62/992,485, filed on Mar. 20, 2020, and to U.S. Provisional Patent Application No. 63/051,093, filed on Jul. 13, 2020. These applications are incorporated herein by reference in their respective entireties.

BACKGROUND INFORMATION

Detecting neural activity in the brain (or any other turbid medium) is useful for medical diagnostics, imaging, neuro-engineering, brain-computer interfacing, and a variety of other diagnostic and consumer-related applications. For example, it may be desirable to detect neural activity in the brain of a user to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

Neural activity and other attributes of the brain may be determined or inferred by measuring responses of tissue within the brain to light pulses. One technique to measure such responses is time-correlated single-photon counting (TCSPC). Time-correlated single-photon counting detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined in order to study the detected neural activity and/or other attributes of the brain.

A photodetector capable of detecting a single photon (i.e., a single particle of optical energy) is an example of a non-invasive detector that can be used in an optical measurement system to detect neural activity within the brain. An exemplary photodetector is implemented by a semiconductor-based single-photon avalanche diode (SPAD), which is capable of capturing individual photons with very high time-of-arrival resolution (a few tens of picoseconds).

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems, circuits, and methods for device enumeration in an optical measurement system are described herein. For example, a processor and/or controller of the system may communicate with devices (e.g., modules and/or detectors) of the system via one or more shared communication buses. Further, the devices may be configured to be modular in the system and thus configured to be added, removed, replaced, relocated, etc. The systems, circuits, and methods described herein may be configured to determine, via an enumeration process, which devices are present in which locations. The systems, circuits, and methods described herein may be further configured to assign addresses to devices in an efficient manner so that components of the systems may communicate with one another via the shared communication bus. Such a device enumeration process may enable the modularity of devices in an optical measurement system, which may allow for flexibility and efficient use of resources.

These and other advantages and benefits of the present systems, circuits, and methods are described more fully herein.

Figure 1:
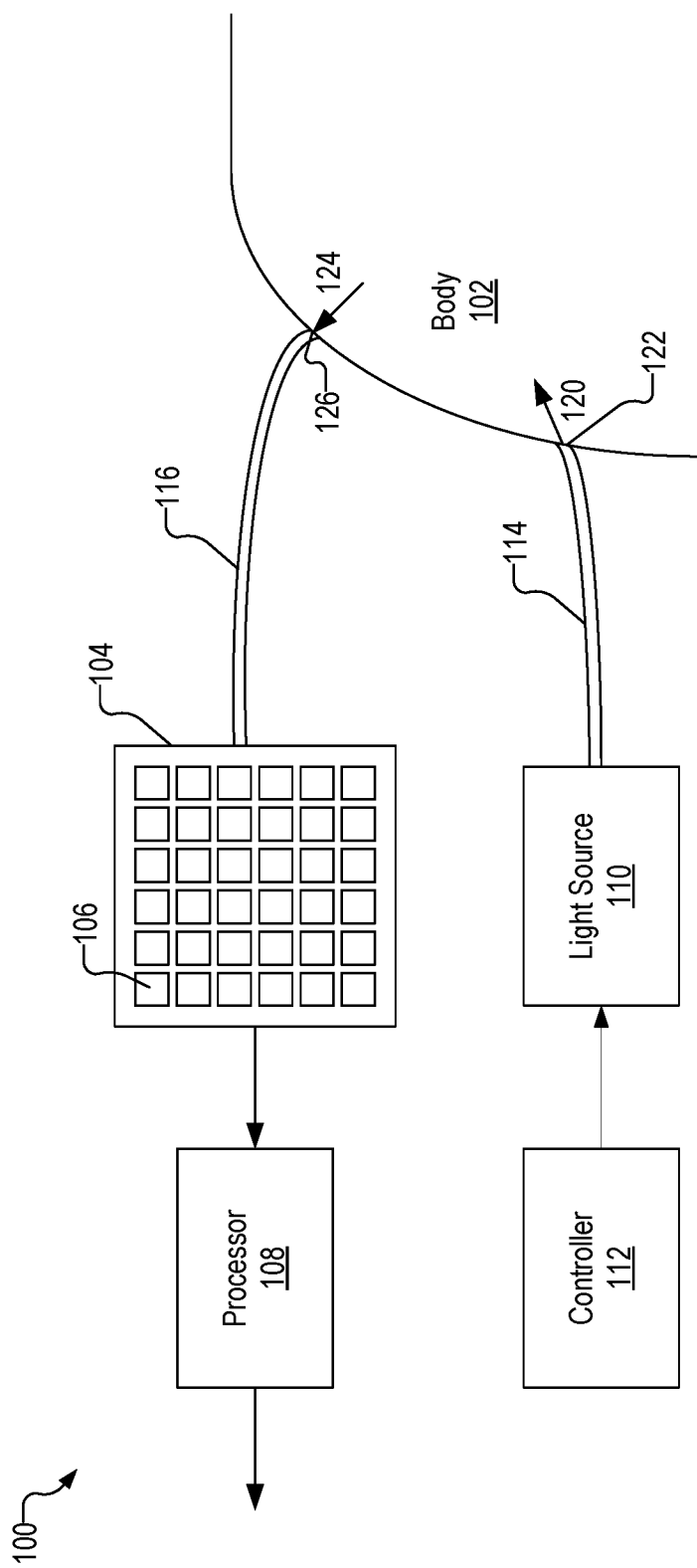
FIG. 1 shows an exemplary optical measurement system.

FIG. 1 shows an exemplary optical measurement system 100 configured to perform an optical measurement operation with respect to a body 102. Optical measurement system 100 may, in some examples, be portable and/or wearable by a user. Optical measurement systems that may be used in connection with the embodiments described herein are described more fully in U.S. patent application Ser. No. 17/176,315, filed Feb. 16, 2021; U.S. patent application Ser. No. 17/176,309, filed Feb. 16, 2021; U.S. patent application Ser. No. 17/176,460, filed Feb. 16, 2021; U.S. patent application Ser. No. 17/176,470, filed Feb. 16, 2021; U.S. patent application Ser. No. 17/176,487, filed Feb. 16, 2021; U.S. patent application Ser. No. 17/176,539, filed Feb. 16, 2021; U.S. patent application Ser. No. 17/176,560, filed Feb. 16, 2021; and U.S. patent application Ser. No. 17/176,466, filed Feb. 16, 2021, which applications are incorporated herein by reference in their entirety.

In some examples, optical measurement operations performed by optical measurement system 100 are associated with a time domain-based optical measurement technique. Example time domain-based optical measurement techniques include, but are not limited to, time-correlated single-photon counting (TCSPC), time domain near infrared spectroscopy (TD-NIRS), time domain diffusive correlation spectroscopy (TD-DCS), and time domain Digital Optical Tomography (TD-DOT). For example, TCSPC detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined in order to study the detected neural activity and/or other attributes of the brain.

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light pipes). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as $2^n$ photodetectors (e.g., 256, 512, . . . , 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes, distributed feedback (DFB) lasers, super luminescent diodes (SLDs), light emitting diodes (LEDs), diode-pumped solid-state (DPSS) lasers, super luminescent light emitting diodes (sLEDs), vertical-cavity surface-emitting lasers (VCSELs), titanium sapphire lasers, micro light emitting diode (mLEDs), and/or any other suitable laser or light source. In some examples, the light emitted by light source 110 is high coherence light (e.g., light that has a coherence length of at least 5 centimeters) at a predetermined center wavelength.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 may travel via an optical conduit 114 (e.g., a light pipe, a light guide, a waveguide, a single-mode optical fiber, and/or or a multi-mode optical fiber) to body 102 of a subject. In cases where optical conduit 114 is implemented by a light guide, the light guide may be spring loaded and/or have a cantilever mechanism to allow for conformably pressing the light guide firmly against body 102.

Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by arrow 120, the light emitted by light source 110 enters body 102 at a first location 122 on body 102. Accordingly, a distal end of optical conduit 114 may be positioned at (e.g., right above or physically attached to) first location 122 (e.g., to a scalp of the subject). In some examples, the light may emerge from optical conduit 114 and spread out to a certain spot size on body 102 to fall under a predetermined safety limit.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a single-mode optical fiber, and/or or a multi-mode optical fiber) is positioned at (e.g., right above or physically attached to) output location 126 on body 102. In this manner, optical conduit 116 may collect light 124 as it exits body 102 at location 126 and carry the light to detector 104. The light may pass through one or more lenses and/or other optical elements (not shown) that direct the light onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., brain tissue, blood flow, etc.) in body 102. Example embodiments of accumulated outputs are described herein.

Figure 2:
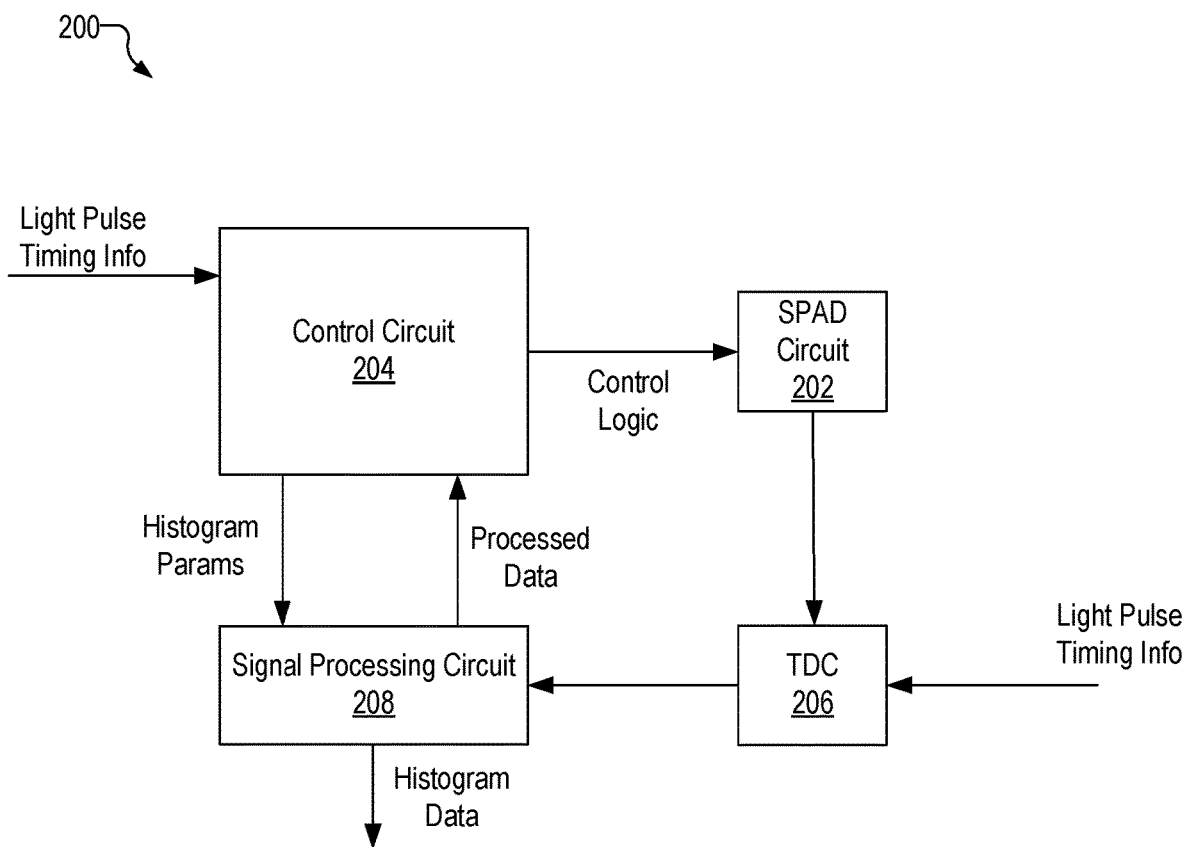
FIG. 2 illustrates an exemplary detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 includes a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may include a capacitor that is pre-charged with a bias voltage before a command is provided to arm the SPAD. Gating the SPAD with a capacitor instead of with an active voltage source, such as is done in some conventional SPAD architectures, has a number of advantages and benefits. For example, a SPAD that is gated with a capacitor may be armed practically instantaneously compared to a SPAD that is gated with an active voltage source. This is because the capacitor is already charged with the bias voltage when a command is provided to arm the SPAD. This is described more fully in U.S. Pat. Nos. 10,158,038 and 10,424,683, which are incorporated herein by reference in their entireties.

In some alternative configurations, SPAD circuit 202 does not include a fast gating circuit. In these configurations, the SPAD included in SPAD circuit 202 may be gated in any suitable manner or be configured to operate in a free running mode with passive quenching.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control a gate delay, which specifies a predetermined amount of time control circuit 204 is to wait after an occurrence of a light pulse (e.g., a laser pulse) to put the SPAD in the armed state. To this end, control circuit 204 may receive light pulse timing information, which indicates a time at which a light pulse occurs (e.g., a time at which the light pulse is applied to body 102). Control circuit 204 may also control a programmable gate width, which specifies how long the SPAD is kept in the armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters. In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Alternatively, a single TDC 206 may be associated with multiple photodetectors 106. Likewise, a single control circuit 204 and a single signal processing circuit 208 may be provided for a one or more photodetectors 106 and/or TDCs 206.

Figure 3:
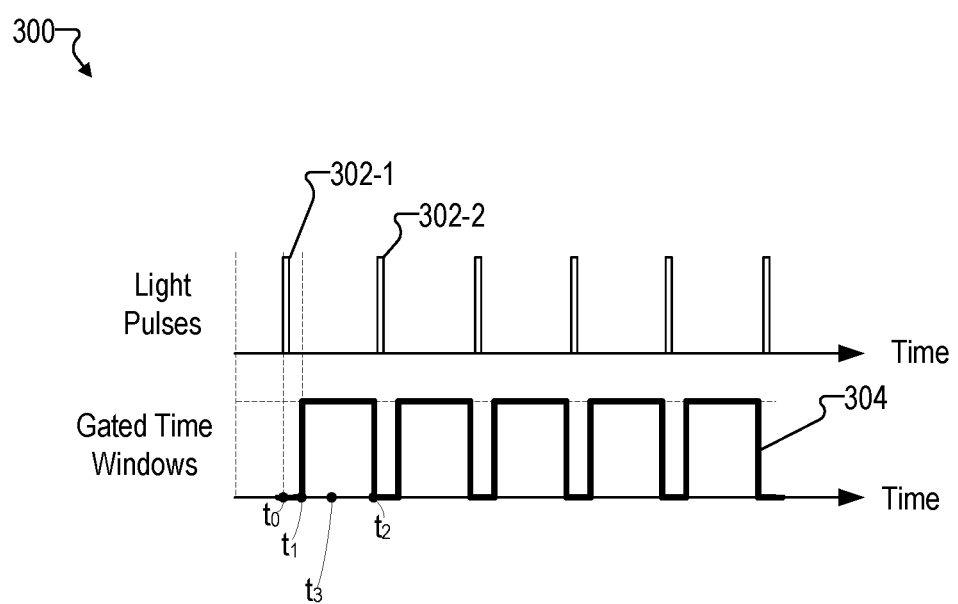
FIG. 3 illustrates an exemplary timing diagram for performing an optical measurement operation using an optical measurement system.

FIG. 3 illustrates an exemplary timing diagram 300 for performing an optical measurement operation using optical measurement system 100. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHz)). The light pulses may be scattered by the target and then detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

For example, timing diagram 300 shows a sequence of light pulses 302 (e.g., light pulses 302-1 and 302-2) that may be applied to the target (e.g., tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON to detect photons. Referring to light pulse 302-1, light pulse 302-1 is applied at a time to. At a time $t_1$, a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time to, which may minimize photons detected directly from the laser pulse, before the laser pulse reaches the target. However, in some alternative examples, time $t_1$ is set to be equal to time to.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time t3, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

As mentioned, in some alternative examples, photodetector 106 may be configured to operate in a free-running mode such that photodetector 106 is not actively armed and disarmed (e.g., at the end of each predetermined gated time window represented by pulse wave 304). In contrast, while operating in the free-running mode, photodetector 106 may be configured to reset within a configurable time period after an occurrence of a photon detection event (i.e., after photodetector 106 detects a photon) and immediately begin detecting new photons. However, only photons detected within a desired time window (e.g., during each gated time window represented by pulse wave 304) may be included in the TPSF.

Figure 4:
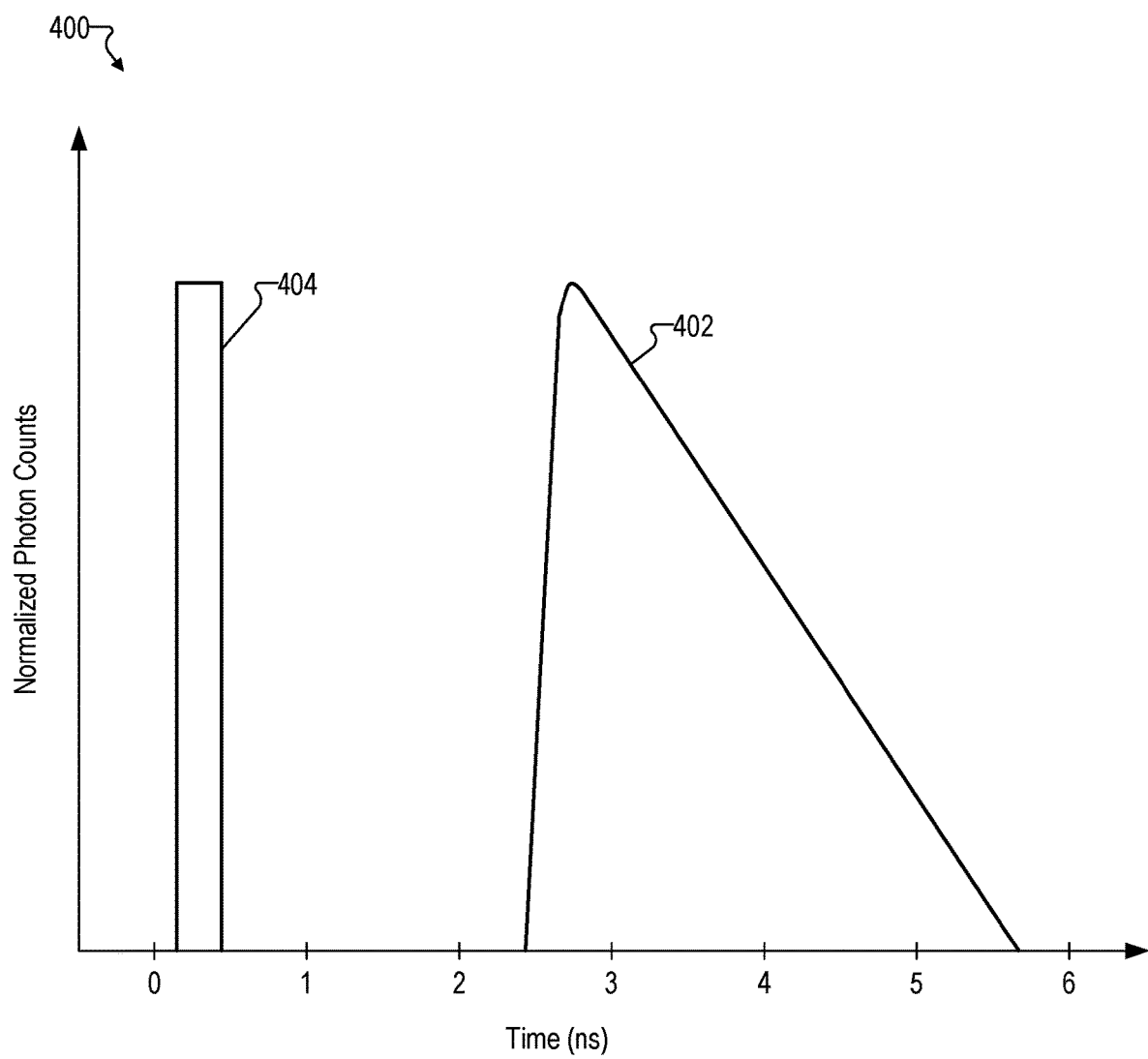
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer detected neural activity.

Optical measurement system 100 may be implemented by or included in any suitable device. For example, optical measurement system 100 may be included, in whole or in part, in a non-invasive wearable device (e.g., a headpiece) that a user may wear to perform one or more diagnostic, imaging, analytical, and/or consumer-related operations. The non-invasive wearable device may be placed on a user's head or other part of the user to detect neural activity. In some examples, such neural activity may be used to make behavioral and mental state analysis, awareness and predictions for the user.

Mental state described herein refers to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, behavior, preferences, or attitude of the user, and the creation, training, and use of neuromes can be found in U.S. Provisional Patent Application No. 63/047,991, filed Jul. 3, 2020. Exemplary measurement systems and methods using biofeedback for awareness and modulation of mental state are described in more detail in U.S. patent application Ser. No. 16/364,338, filed Mar. 26, 2019, published as US2020/0196932A1. Exemplary measurement systems and methods used for detecting and modulating the mental state of a user using entertainment selections, e.g., music, film/video, are described in more detail in U.S. patent application Ser. No. 16/835,972, filed Mar. 31, 2020, published as US2020/0315510A1. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, published as US2020/0337624A1. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

Figure 5:
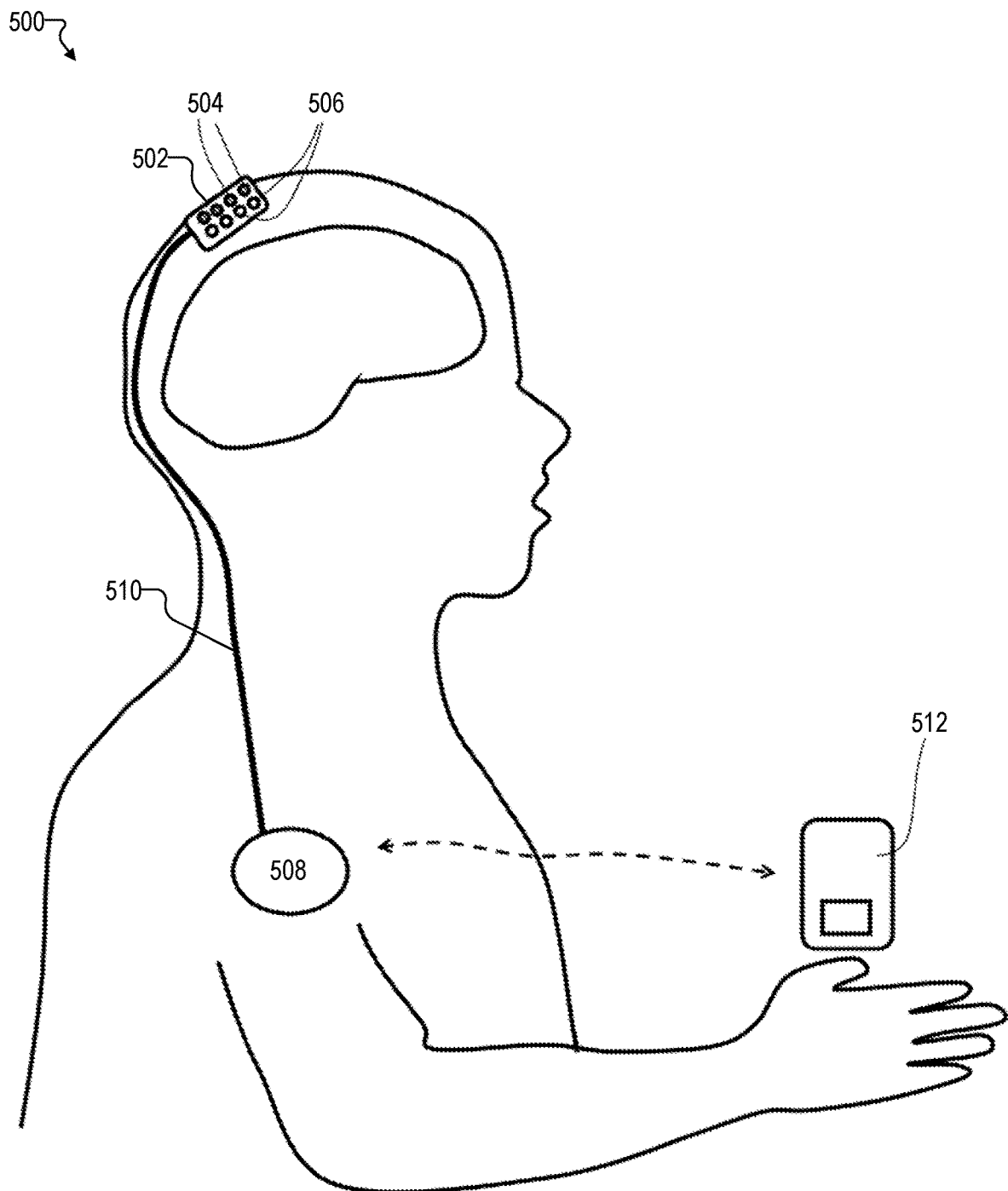
FIG. 5 shows an exemplary non-invasive wearable brain interface system.

FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be attached to a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. Head-mountable component 502 may be made out of any suitable cloth, soft polymer, plastic, hard shell, and/or any other suitable material as may serve a particular implementation. Examples of headgears used with wearable brain interface systems are described more fully in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and for transforming photodetector measurements into an intensity value that represents an optical property of a target within the brain. Brain interface system 500 allows optical detection of deep anatomical locations beyond skin and bone (e.g., skull) by extracting data from photons originating from light source 506 and emitted to a target location within the user's brain, in contrast to conventional imaging systems and methods (e.g., optical coherence tomography (OCT)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by detector 504 may be included elsewhere in brain interface system 500. For example, a light source may be included in processor 508 and coupled to head mountable component 502 through optical connections.

Optical measurement system 100 may alternatively be included in a non-wearable device (e.g., a medical device and/or consumer device that is placed near the head or other body part of a user to perform one or more diagnostic, imaging, and/or consumer-related operations). Optical measurement system 100 may alternatively be included in a sub-assembly enclosure of a wearable invasive device (e.g., an implantable medical device for brain recording and imaging).

Optical measurement system 100 may be modular in that one or more components of optical measurement system 100 may be removed, changed out, or otherwise modified as may serve a particular implementation. Additionally or alternatively, optical measurement system 100 may be modular such that one or more components of optical measurement system 100 may be housed in a separate housing (e.g., module) and/or may be movable relative to other components. Exemplary modular multimodal measurement systems are described in more detail in U.S. patent application Ser. No. 17/176,460, filed Feb. 16, 2021, U.S. patent application Ser. No. 17/176,470, filed Feb. 16, 2021, U.S. patent application Ser. No. 17/176,487, filed Feb. 16, 2021, U.S. Provisional Patent Application No. 63/038,481, filed Jun. 12, 2020, and U.S. patent application Ser. No. 17/176,560, filed Feb. 16, 2021, which applications are incorporated herein by reference in their respective entireties.

Figure 6:
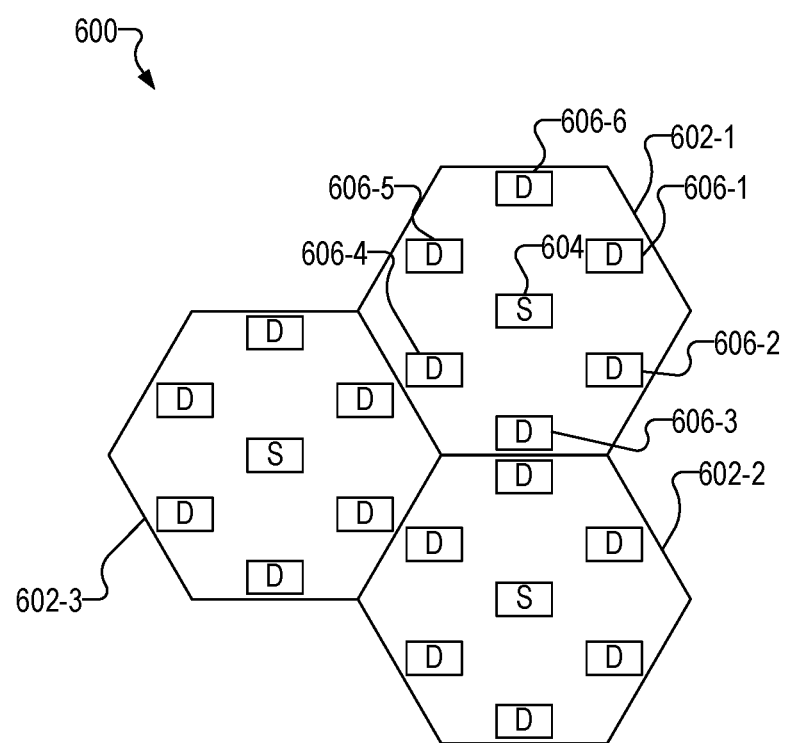
FIG. 6 shows an exemplary wearable module assembly.

To illustrate, FIG. 6 shows an exemplary wearable module assembly 600 ("assembly 600") that implements one or more of the optical measurement features described herein. Assembly 600 may be worn on the head or any other suitable body part of the user. As shown, assembly 600 may include a plurality of modules 602 (e.g., modules 602-1 through 602-3). While three modules 602 are shown to be included in assembly 600 in FIG. 6, in alternative configurations, any number of modules 602 (e.g., a single module up to sixteen or more modules) may be included in assembly 600. Moreover, while modules 602 are shown to be adjacent to and touching one another, modules 602 may alternatively be spaced apart from one another (e.g., in implementations where modules 602 are configured to be inserted into individual slots or cutouts of the headgear). Moreover, while modules 602 are shown to have a hexagonal shape, modules 602 may alternatively have any other suitable geometry (e.g., in the shape of a pentagon, octagon, square, rectangular, circular, triangular, free-form, etc.). Assembly 600 may conform to three-dimensional surface geometries, such as a user's head. Exemplary wearable module assemblies comprising a plurality of wearable modules are described in more detail in U.S. Provisional Patent Application No. 62/992,550, filed Mar. 20, 2020, and U.S. Provisional Patent Application No. 63/038,458, filed Jun. 12, 2020, which applications are incorporated herein by reference in their respective entireties.

The wearable module assembly 600 may also conform to three-dimensional surface geometries, such as a user's head. Exemplary wearable module assemblies comprising a plurality of wearable modules are described in more detail in U.S. Provisional Patent Application No. 62/992,550, filed Mar. 20, 2020, which application is incorporated herein by reference in its entirety.

Each module 602 includes a source 604 and a plurality of detectors 606 (e.g., detectors 606-1 through 606-6). Source 604 may be implemented by one or more light sources similar to light source 110. Each detector 606 may implement or be similar to detector 104 and may include a plurality of photodetectors (e.g., SPADs) as well as other circuitry (e.g., TDCs). As shown, detectors 606 are arranged around and substantially equidistant from source 604. In other words, the spacing between a light source (i.e., a distal end portion of a light source optical conduit) and the detectors (i.e., distal end portions of optical conduits for each detector) are maintained at the same fixed distance on each module to ensure homogeneous coverage over specific areas and to facilitate processing of the detected signals. The fixed spacing also provides consistent spatial (lateral and depth) resolution across the target area of interest, e.g., brain tissue. Moreover, maintaining a known distance between the light emitter and the detector allows subsequent processing of the detected signals to infer spatial (e.g., depth localization, inverse modeling) information about the detected signals. Detectors 606 may be alternatively disposed as may serve a particular implementation. Exemplary wearable module assemblies with integrated detectors and other module components are described in more detail in U.S. Provisional Patent Application No. 63/038,458, filed Jun. 12, 2020, which application is incorporated herein by reference in its entirety.

Figure 7:
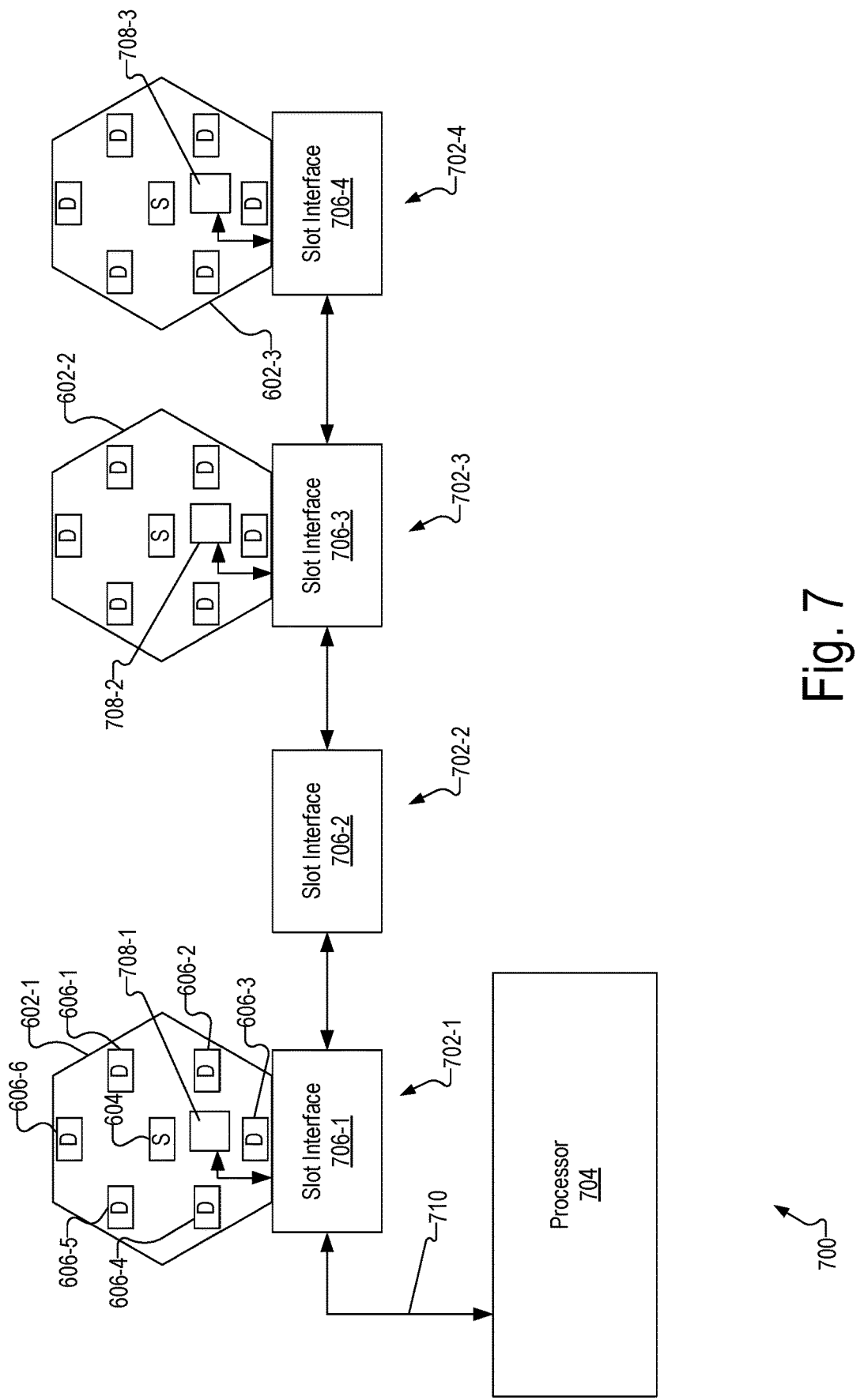
FIGS. 7-8 show exemplary configurations of a wearable module assembly.

FIG. 7 shows an exemplary configuration 700 of components of an optical measurement system (e.g., optical measurement system 100). Configuration 700 shows modules 602 (e.g., modules 602-1 through 602-3, shown in FIG. 6) in an implementation where modules 602 are configured to be inserted into individual slots 702 (e.g., slots 702-1 through 702-4) of a wearable device (e.g., head-mountable component 502 shown in FIG. 5 or any other suitable component configured to be worn by a user). While configuration 700 shows three modules 602 in four slots 702, any suitable number of modules and slots may be included in configuration 700.

Configuration 700 also includes a processor 704 (e.g., an implementation of processor 108 and/or processor 508) that is configured to communicate with modules 602 via slot interfaces 706 (e.g., slot interfaces 706-1 through 706-4) of each slot 702. Configuration 700 also shows modules 602 each including a control circuit 708 (e.g., control circuits 708-1 through 708-3) configured to communicate with processor 704. Configuration 700 also includes a communication bus 710 through which processor 704 may transmit and receive data (e.g., signals, messages, commands, information, etc.) to and from modules 602.

Optical measurement system 100 may be configured to be a modular system, such that modules 602 may be interchangeable in slots 702. For example, in configuration 700, module 602-1 is located in slot 702-1, module 602-2 is located in slot 702-3, and module 602-3 is located in slot 702-4. In other configurations, each of modules 602 may be located in different slots 702, fewer modules may be located in slots 702, or more modules may be located in slots 702. To illustrate, a user may rearrange modules 602 such that they are located in different slots 702. For example, the user may place module 602-1 in slot 702-2 instead of in slot 702-1.

Processor 704 may be configured to determine which modules 602 are located in which slots 702 so that processor 704 may communicate individually with each of modules 602 and/or each of detectors 606 of modules 602. Furthermore, processor 704 may be configured to assign address identifiers to each of detectors 606 so that processor 704 may transmit data to and/or receive data from specific detectors 606. As communication bus 710 may, in some examples, be configured as a shared communication bus through which slot interfaces 706 are connected serially to processor 704, such address identifiers may enable processor 704 to specify detectors 606 for transmitting data and identify from which of detectors 606 data is received.

For instance, processor 704 may perform an enumeration process (e.g., during a startup phase) for enumerating modules 602 and/or detectors 606. During the enumeration process, processor 704 may successively transmit a command (also referred to herein as an "enable command") to each slot included in slots 702 to enable a respective module 602 located at that slot if the slot is housing a module. For example, processor 704 may first transmit the enable command to slot 702-1. As module 602-1 is located at slot 702-1, module 602-1 may be enabled in response to the command. Processor 704 may then transmit the enable command to slot 702-2. However, as shown in the particular example of FIG. 7, there is no module at slot 702-2 in configuration 700, therefore, no module would be enabled. Processor 704 may then transmit the enable command to slot 702-3. As module 602-2 is located at slot 702-3, module 602-2 may be enabled in response to the command. Processor 704 may similarly successively transmit the enable command to the remainder of slots 702.

If a module is located at a slot when processor 704 transmits the enable command to the slot, a control circuit of the module may transmit an acknowledgement (e.g., an acknowledgement signal) back to processor 704, thereby indicating that the module is located at the slot and that the module has been enabled. For instance, in response to the enable command transmitted by processor 704 to slot 702-1, control circuit 708-1 of module 602-1 may transmit an acknowledgment to processor 704 indicating that module 602-1 is located at slot 702-1 and enabled. Based on the acknowledgement, processor 704 may determine that module 602-1 is located at slot 702-1.

Once processor 704 determines that module 602-1 is located at slot 702-1, processor 704 may successively transmit a plurality of detector address identifiers that are to be assigned to each detector 606 of module 602-1. This transmission may be performed in any suitable manner. For example, as described in more detail below, processor 704 may transmit the detector address identifiers by broadcasting the detector address identifiers by way of communication bus 710 to all of slots 702.

Each detector address identifier transmitted by processor 704 may be based on a slot location of slot 702-1 and a detector location on module 602. As modules 602 each include six detectors in this example, detector address identifiers may be 0101 (for slot 1, detector 1), 0102, 0103, 0104, 0105, and 0106 for detectors 606-1 through 606-6, respectively. Any other suitable addresses/addressing scheme may be used.

Concurrent with the transmission of the detector address identifiers, control circuit 708-1 may direct each of detectors 606 to successively be placed in an enumeration mode in which each detector 606 is assigned a different detector address identifier of the detector address identifiers. As communication bus 710 may be a shared communication bus and detectors 606 have yet to be assigned addresses for direct communication, processor 704 may transmit the detector address identifiers by broadcasting the detector address identifiers on communication bus 710. Thus, any of detectors 606 that are in the enumeration mode may receive the detector address identifier being broadcast and be assigned the detector address identifier. Control circuit 708-1 may therefore coordinate with processor 704 such that a correct detector 606 is in the enumeration mode while processor 704 is broadcasting a corresponding detector address identifier.

For example, control circuit 708-1 may place detector 606-1 in the enumeration mode while processor 704 is transmitting detector address identifier 0101. Detector 606-1 may accordingly be assigned detector address identifier 0101. For instance, detector 606-1 may store the detector address identifier in a memory of detector 606-1 and may respond to commands received that include the detector address identifier. Detector 606-1 may also include the detector address identifier in messages transmitted by detector 606-1.

After detector 606-1 has been assigned a detector address identifier, control circuit 708-1 may place detector 606-2 in the enumeration mode while processor 704 is transmitting detector address identifier 0102, and so forth with detectors 606-3 through 606-6. This coordination of placing detectors in the enumeration mode by control circuit 708-1 while a corresponding detector address identifier is broadcast by processor 704 may be implemented in any suitable manner. For instance, processor 704 and control circuit 708-1 may use a predetermined time period for each detector 606 to be placed successively in the enumeration mode as processor 704 successively transmits the detector address identifiers. Additionally or alternatively, control circuit 708-1 and/or detectors 606 may transmit an acknowledgment and/or other messages to processor 704 once a particular detector address identifier is assigned to a detector 600 so that processor 704 may transmit a next detector address identifier for a next detector 606. Any other suitable coordination scheme may be used.

Once detectors 606-1 through 606-6 on module 602-1 have been assigned detector address identifiers, processor 704 may transmit an enable command to a next slot 702-2. As described, as there is no module located in slot 702-2 in the particular example of FIG. 7, processor 704 may receive no acknowledgment to the enable command. Based on the absence of the acknowledgment, processor 704 may determine that no module is located in slot 702-2.

Processor 704 may then transmit an enable command to a next slot 702-3. Control circuit 708-2 may receive the command to enable module 602-2 and the enumeration process may be performed for detectors on module 602-2 as described with module 602-1. The process may be repeated successively for each module 602 at each slot 702. As a result, processor 704 may determine which of slots 702 have modules 602 and also may assign each detector 606 on each module 602 a unique detector address identifier.

In some examples, upon receiving an enable command, a control circuit (e.g., control circuit 708-1) of a module (e.g., module 602-1) may transmit (in addition to or as the acknowledgment) information associated with the module, such as a module identifier (e.g., a serial number of the module and/or any other identifying information or other information associated with the module). Processor 704 may receive such information and base the detector address identifiers on the information.

Additionally or alternatively, detector address identifiers may be based on predetermined slot address identifiers. Slot address identifiers may be assigned in any suitable manner, such as an order on communication bus 710 from processor 704, a location or area on a body of a user for which each slot 702 on the wearable device is configured to be proximate to, etc. In some examples, slots 702 may be configured to house modules 602 in a predetermined orientation (e.g., based on a connection port location, using keyed modules, etc.). Detector address identifiers may thus be further based on a location or position of detector 606 on module 602 and/or a more specific location or area on the body of the user to which detector 606 is configured to be proximate.

In some examples, processor 704 may transmit additional setup information in addition to the detector address identifier to each detector in the enumeration mode. For instance, processor 704 may transmit data representative of a communication mode (e.g., a serial peripheral interface (SPI) mode, etc.) that is to be used for a duration of a session, e.g., a module calibration session, a module testing session, photon detection session when a user is wearing the non-invasive wearable brain interface system 500, or any other type of session when using, testing, or calibrating the non-invasive wearable brain interface system 500. Any other suitable setup information may be provided by processor 704 to each detector in the enumeration mode.

Figure 8:
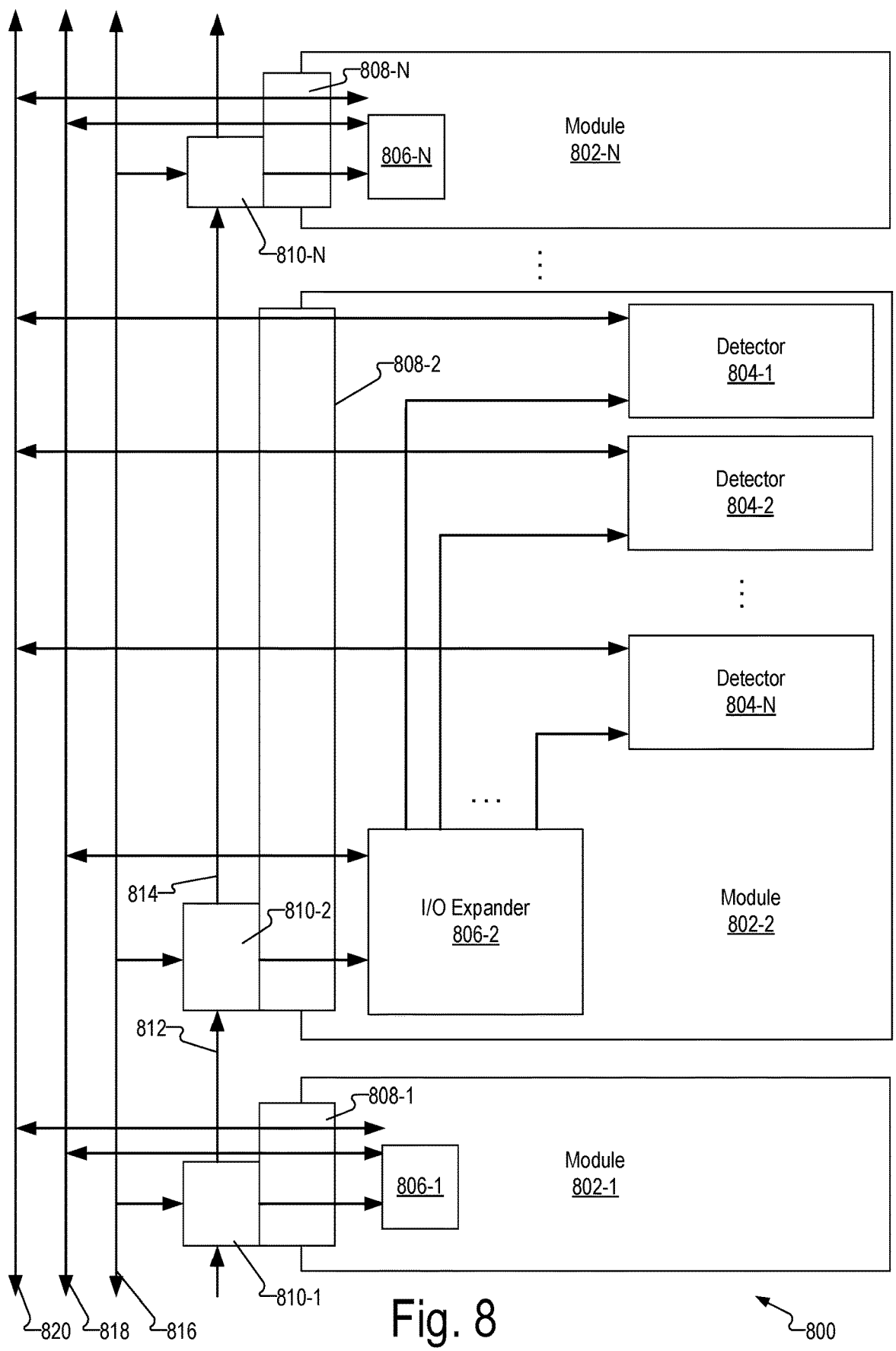

FIG. 8 shows another exemplary configuration 800 that may be an implementation of configuration 700 shown in FIG. 7. Configuration 800 shows modules 802 (e.g., module 802-1 through 802-N) configured to be housed in slots (e.g., slots 702) of a wearable device. Modules 802 may be similar to modules 602 as described in connection with FIGS. 6 and 7.

As shown, module 802-2 includes a plurality of detectors 804 (e.g., detectors 804-1 through 804-N). Each detector 804 may be similar to detectors 606 as described in connection with FIGS. 6 and 7. Though not shown, other modules 802 may also include a plurality of detectors.

Each module 802 may also include an input/output (I/O) expander 806 (e.g., I/O expander 806-1 through 806-N). Each I/O expander 806 may be an implementation of control circuit 708 or a portion of control circuit 708. Each I/O expander 806 may be configured to communicate with a processor (e.g., processor 704, not shown in FIG. 8) via a harness connector 808 (e.g., harness connectors 808-1 through 808-N) and a board scan chain element 810 (e.g., board scan chain element 810-1 through 810-N), which may implement slot interface 706.

In configuration 800, processor 704 may successively transmit the enable command to each slot 702 by utilizing a scan chain configured to successively enable a respective I/O expander 806 via a respective board scan chain element 810 for each slot 702 if a module is located at the slot. Each board scan chain element 810 receives a scan input 812 from a previous board scan chain element in the scan chain (e.g., board scan chain element 810-2 receives scan input 812 from board scan chain element 810-1) and provides a scan output 814 to a next board scan chain element (e.g., board scan chain element 810-3 (not shown)) in the scan chain.

Board scan chain element 810 further receives a scan clock signal 816. Based on scan input 812, scan output 814, and scan clock signal 816, the scan chain enables each I/O expander 806 of each module 802 successively in each slot 702.

For instance, when I/O expander 806-2 is enabled, I/O expander 806-2 may communicate with processor 704 via a shared enumeration bus 818 (e.g., a sideband channel of communication bus 710, a separate shared communication bus, or any other suitable implementation) to coordinate enabling of detectors 804 to receive detector address identifiers. As I/O expander 806-2 receives signals from processor 704, I/O expander 806-2 is configured to provide signals to each of detectors 804 to successively enable each detector 804. When a detector 804 (e.g., detector 804-1) is enabled, the detector 804 may communicate with processor 704 via a shared data bus 820 (e.g., a main channel of communication bus 710, a separate shared communication bus, or any other suitable implementation) to receive the detector address identifier being broadcast by processor 704. As described, I/O expander 806-2 may coordinate with processor 704 such that each of detectors 804 are successively placed in an enumeration mode to be assigned a corresponding detector address identifier of a plurality of detector address identifiers successively broadcast on shared data bus 820.

Once detectors 804 are assigned detector address identifiers, processor 704 may communicate individually with specific detectors 804 via shared data bus 820 by addressing messages with the detector address identifier of the specific detector 804. Messages received by processor 704 via shared data bus 820 may also include specific detector address identifiers so that processor 704 may identify which detector 804 transmitted the messages.

In some examples, processor 704 may be configured to continue broadcasting certain messages to all detectors 804 using a particular broadcast address (e.g., all zeros (0) or any other suitable broadcast address). Additionally or alternatively, processor 704 may be configured to send messages to groups of detectors (e.g., all detectors on a specific module, all detectors in a specific area or region, etc.) using particular addresses and/or portions of addresses. For instance, detectors 804 on module 802-2 may all begin with a specific number or set of numbers that indicate that the detectors are on module 802-2. A message for all detectors on module 802-2 may then, for instance, include an address that starts with the specific number or set of numbers followed by all zeros (0). Any other suitable message addressing schemes may be used to communicate with detectors 804 and/or modules 802.

FIGS. 9-14 illustrate embodiments of a wearable device 900 that includes elements of the optical detection systems described herein. In particular, the wearable devices 900 shown in FIGS. 9-14 include a plurality of modules 902, similar to the modules shown in FIG. 6 as described herein. For example, each module 902 includes a source 604 and a plurality of detectors 606 (e.g., detectors 606-1 through 606-6). Source 604 may be implemented by one or more light sources similar to light source 110. Each detector 606 may implement or be similar to detector 104 and may include a plurality of photodetectors. The wearable devices 900 may each also include a controller (e.g., controller 112) and a processor (e.g., processor 108) and/or be communicatively connected to a controller and processor. In general, wearable device 900 may be implemented by any suitable headgear and/or clothing article configured to be worn by a user. The headgear and/or clothing article may include batteries, cables, and/or other peripherals for the components of the optical measurement systems described herein.

Figure 9:
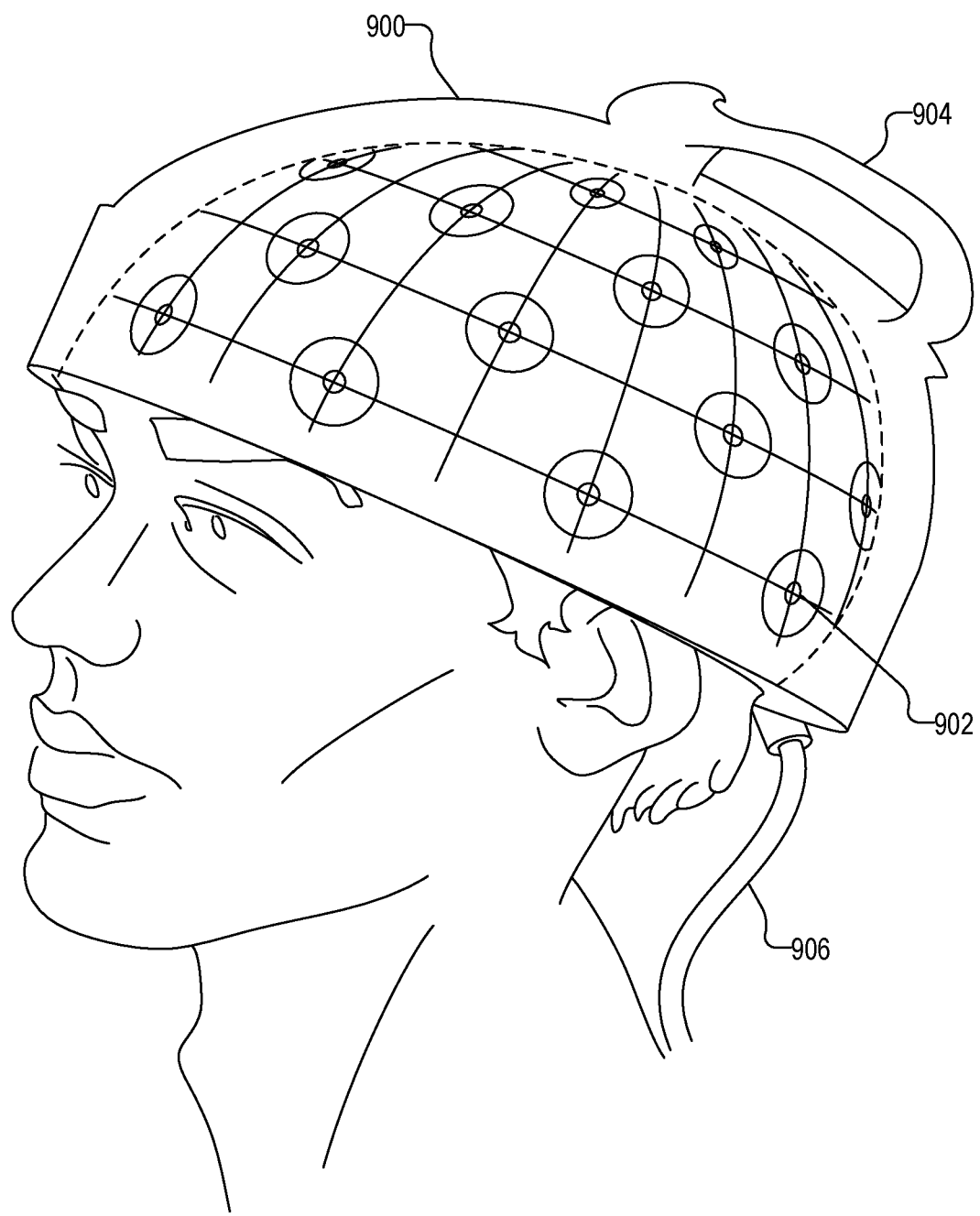
FIGS. 9-14 illustrate embodiments of a wearable device that includes elements of the optical measurement systems described herein.
Figure 10:
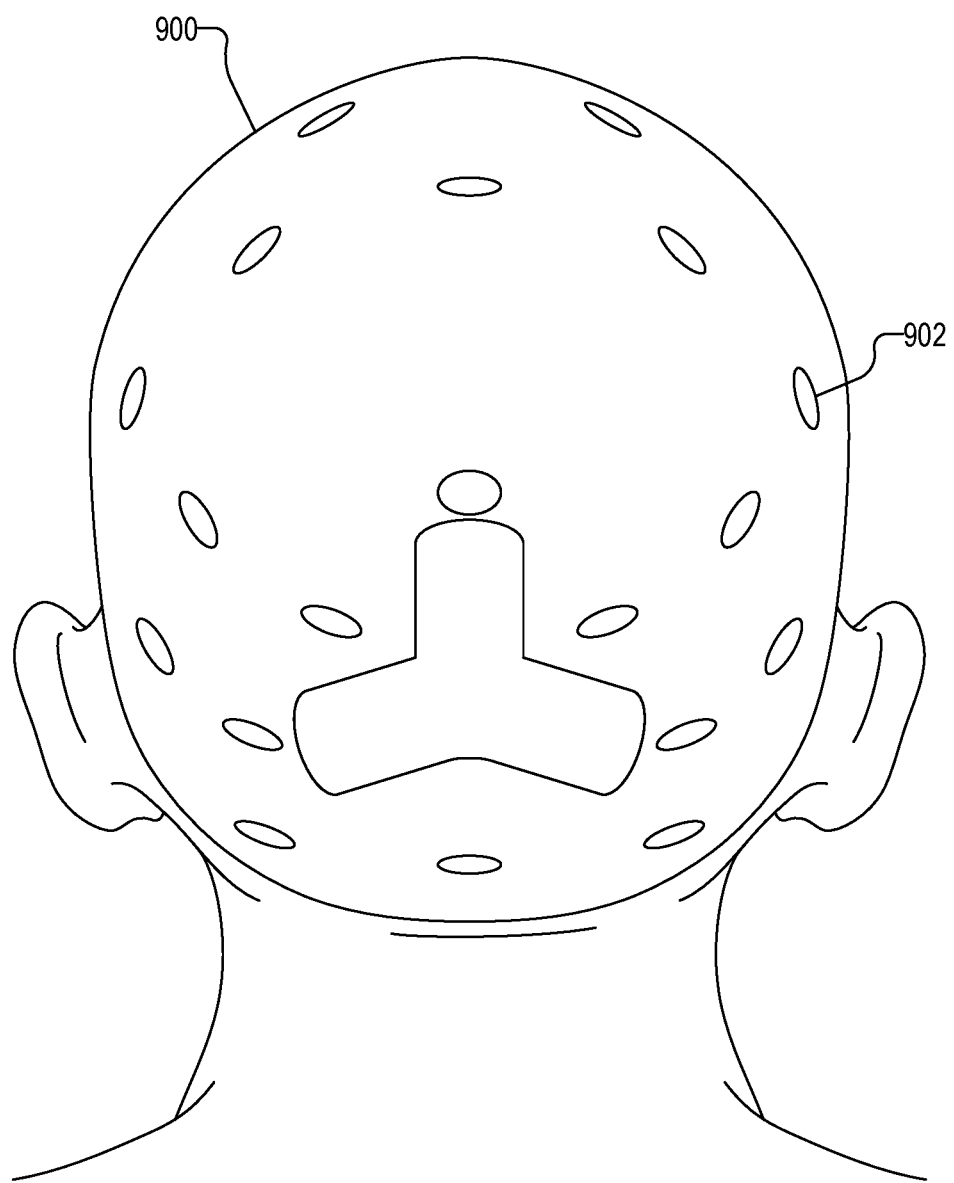
Figure 11:
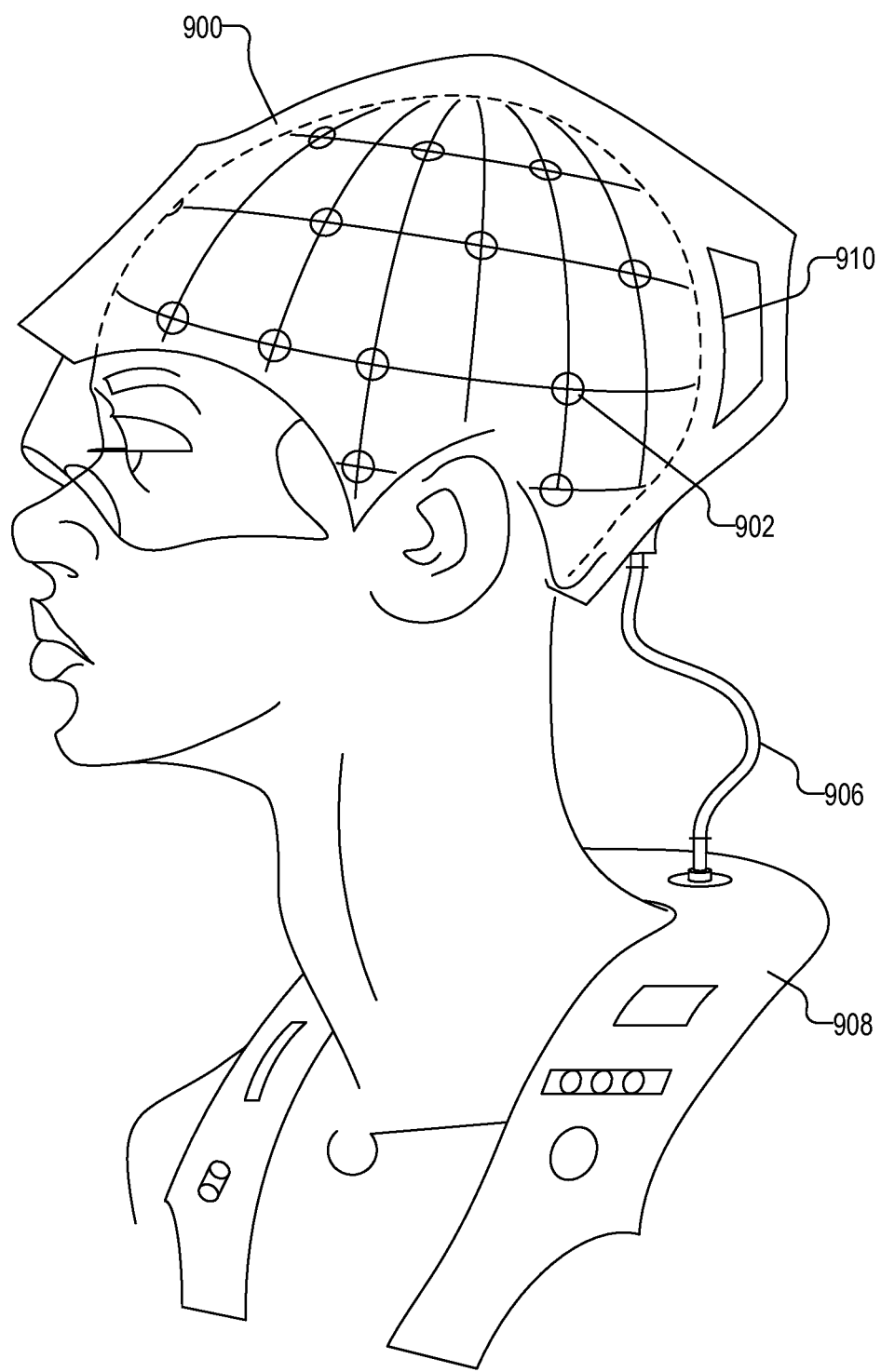

FIG. 9 illustrates an embodiment of a wearable device 900 in the form of a helmet with a handle 904. A cable 906 extends from the wearable device 900 for attachment to a battery or hub (with components such as a processor or the like). FIG. 10 illustrates another embodiment of a wearable device 900 in the form of a helmet showing a back view. FIG. 11 illustrates a third embodiment of a wearable device 900 in the form of a helmet with the cable 906 leading to a wearable garment 908 (such as a vest or partial vest) that can include a battery or a hub. Alternatively or additionally, the wearable device 900 can include a crest 910 or other protrusion for placement of the hub or battery.

Figure 12:
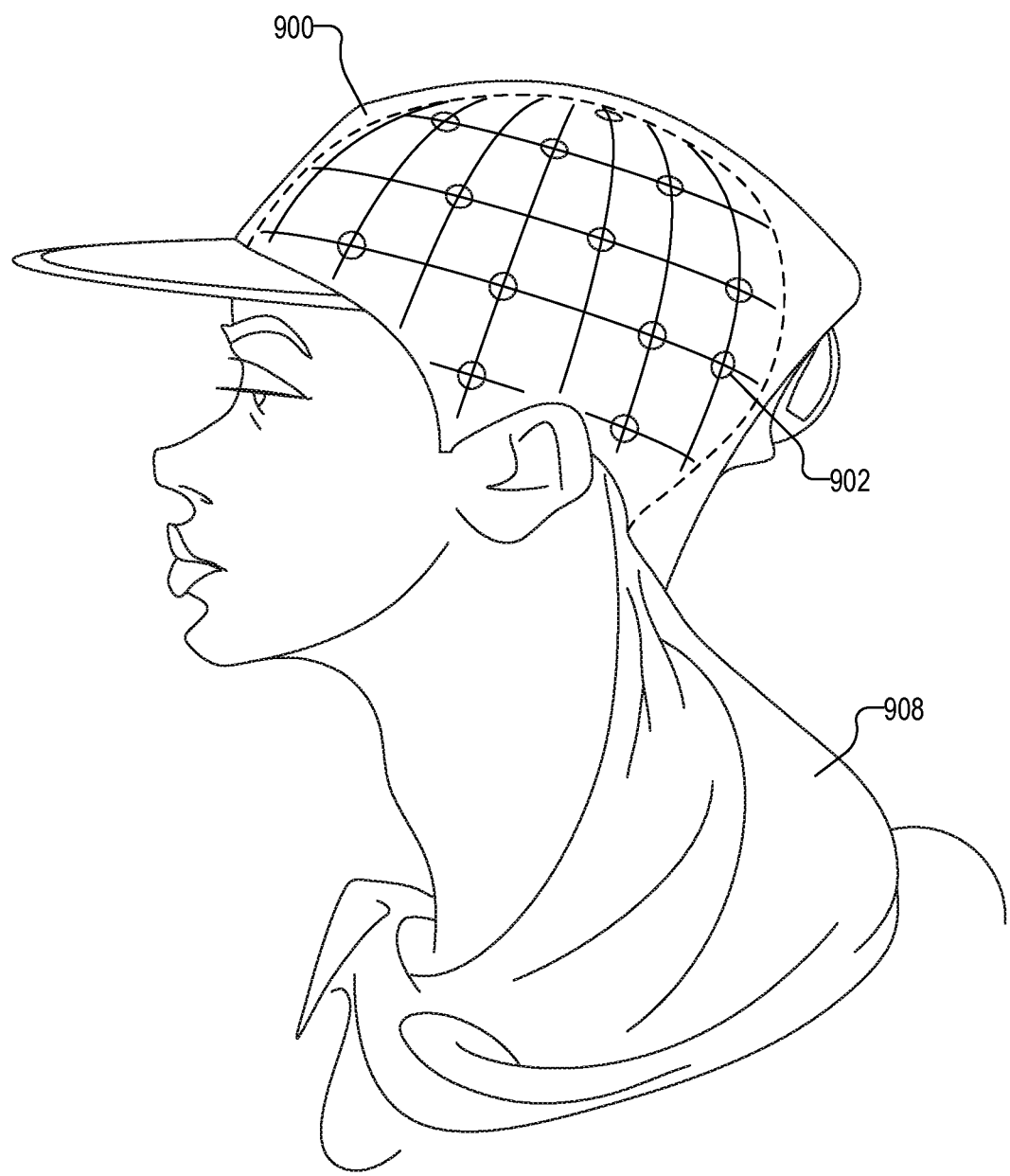
Figure 13:
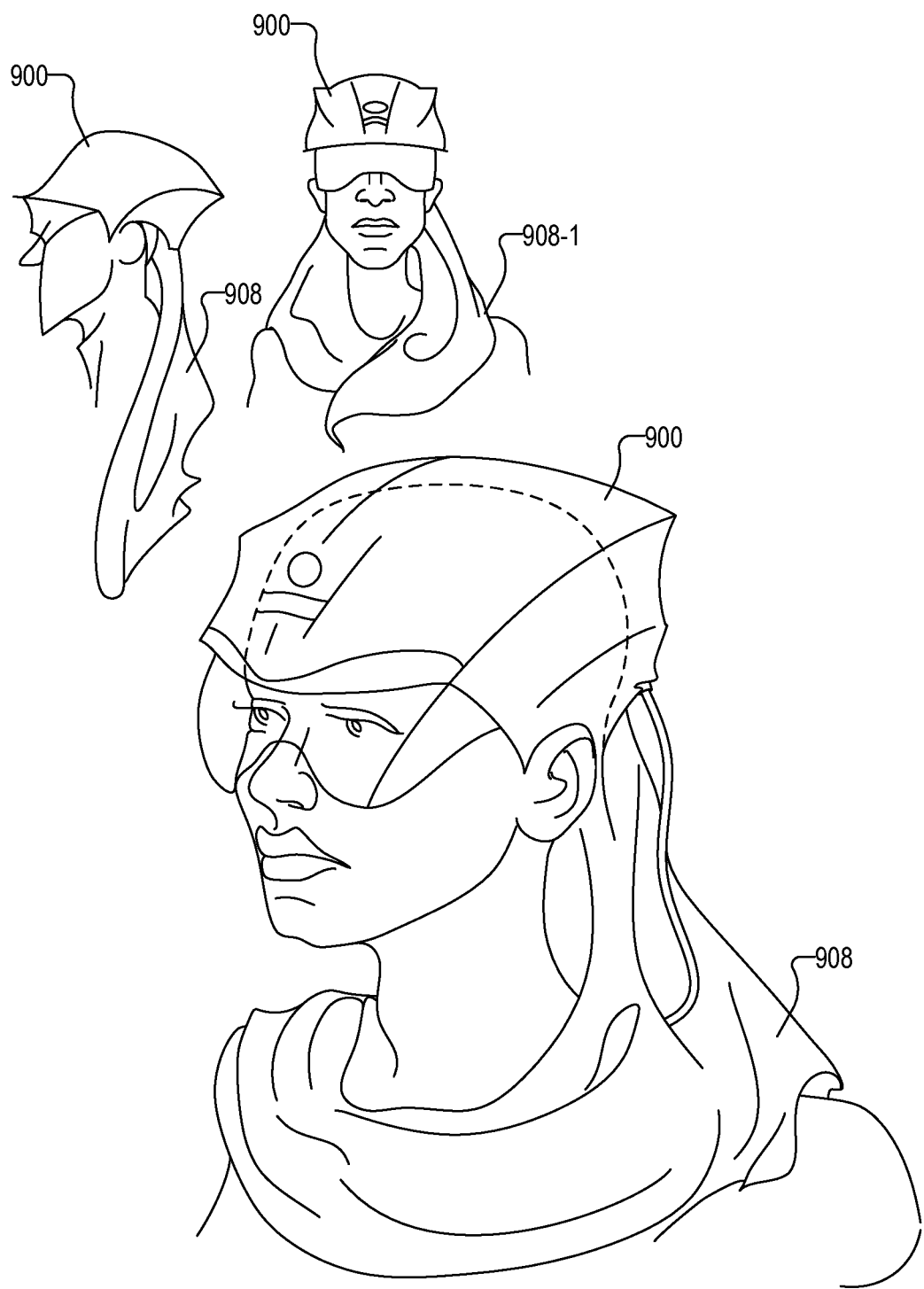
Figure 14:
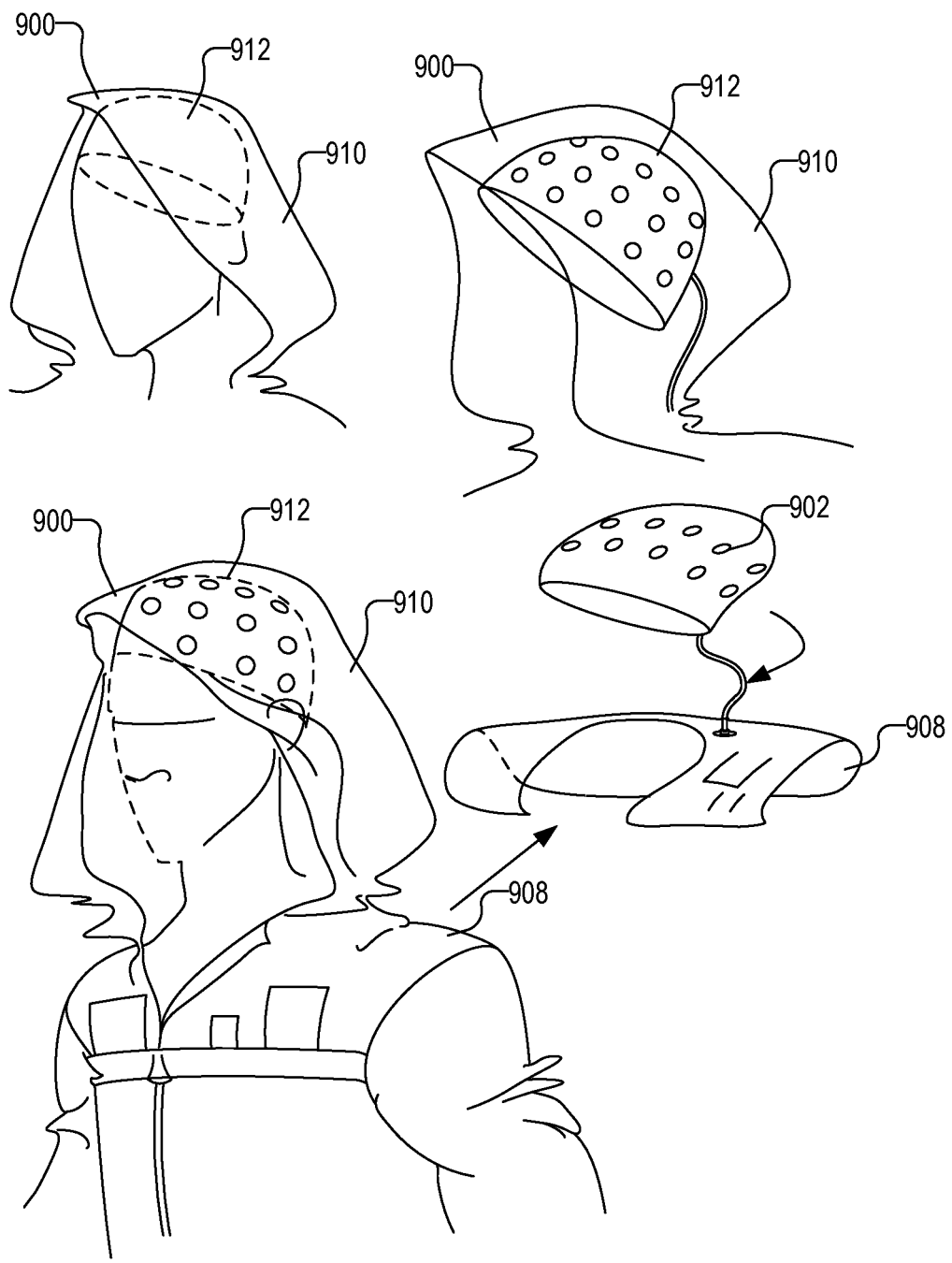

FIG. 12 illustrates another embodiment of a wearable device 900 in the form of a cap with a wearable garment 908 in the form of a scarf that may contain or conceal a cable, battery, and/or hub. FIG. 13 illustrates additional embodiments of a wearable device 900 in the form of a helmet with a one-piece scarf 908 or two-piece scarf 908-1. FIG. 14 illustrates an embodiment of a wearable device 900 that includes a hood 910 and a beanie 912 which contains the modules 902, as well as a wearable garment 908 that may contain a battery or hub.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 15:
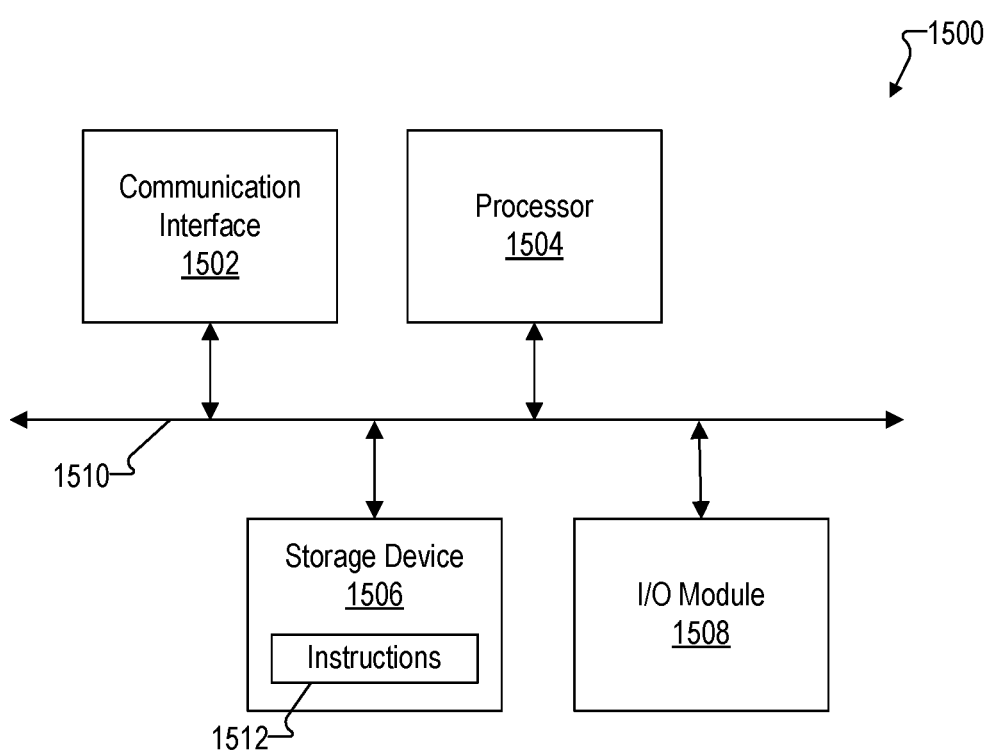
FIG. 15 illustrates an exemplary computing device.

FIG. 15 illustrates an exemplary computing device 1500 that may be specifically configured to perform one or more of the processes described herein. Any of the systems, units, computing devices, and/or other components described herein may be implemented by computing device 1500.

As shown in FIG. 15, computing device 1500 may include a communication interface 1502, a processor 1504, a storage device 1506, and an input/output ("I/O") module 1508 communicatively connected one to another via a communication infrastructure 1510. While an exemplary computing device 1500 is shown in FIG. 15, the components illustrated in FIG. 15 are not intended to be limiting. Additional or alternative components may be used in other embodiments. Components of computing device 1500 shown in FIG. 15 will now be described in additional detail.

Communication interface 1502 may be configured to communicate with one or more computing devices. Examples of communication interface 1502 include, without limitation, a wired network interface (such as a network interface card), a wireless network interface (such as a wireless network interface card), a modem, an audio/video connection, and any other suitable interface.

Processor 1504 generally represents any type or form of processing unit capable of processing data and/or interpreting, executing, and/or directing execution of one or more of the instructions, processes, and/or operations described herein. Processor 1504 may perform operations by executing computer-executable instructions 1512 (e.g., an application, software, code, and/or other executable data instance) stored in storage device 1506.

Storage device 1506 may include one or more data storage media, devices, or configurations and may employ any type, form, and combination of data storage media and/or device. For example, storage device 1506 may include, but is not limited to, any combination of the non-volatile media and/or volatile media described herein. Electronic data, including data described herein, may be temporarily and/or permanently stored in storage device 1506. For example, data representative of computer-executable instructions 1512 configured to direct processor 1504 to perform any of the operations described herein may be stored within storage device 1506. In some examples, data may be arranged in one or more databases residing within storage device 1506.

I/O module 1508 may include one or more I/O modules configured to receive user input and provide user output. I/O module 1508 may include any hardware, firmware, software, or combination thereof supportive of input and output capabilities. For example, I/O module 1508 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1508 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1508 is configured to provide graphical data to a display for presentation to a user. The graphical data may be representative of one or more graphical user interfaces and/or any other graphical content as may serve a particular implementation.

Figure 16:
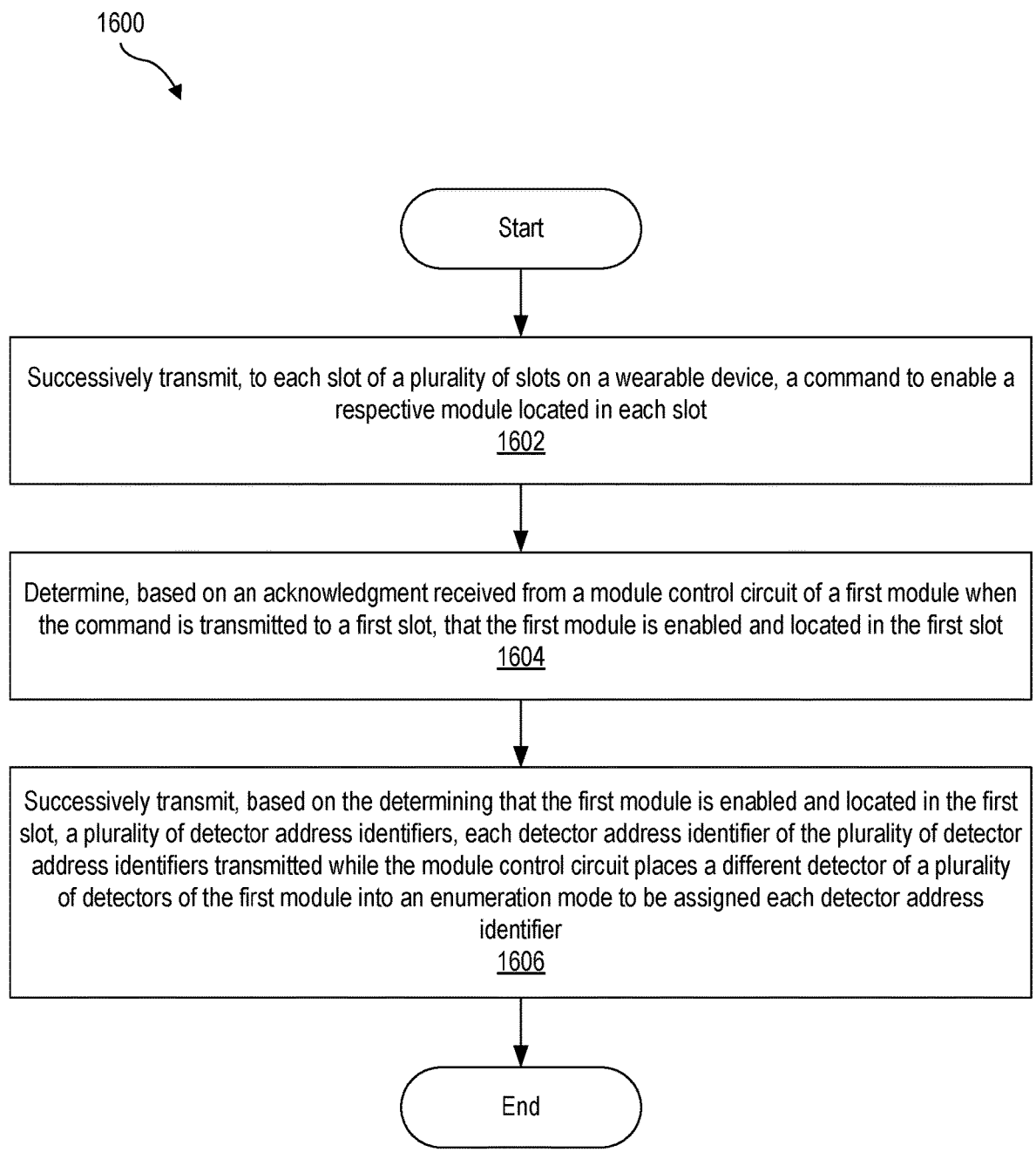
FIG. 16 illustrates an exemplary method.

FIG. 16 illustrates an exemplary method 1600 that may be performed by processor 704 and/or any implementation thereof. While FIG. 16 illustrates exemplary operations according to one embodiment, other embodiments may omit, add to, reorder, and/or modify any of the operations shown in FIG. 16. Each of the operations shown in FIG. 16 may be performed, or repeated as needed for each respective module located in its respective slot on the wearable device, in any of the ways described herein.

In operation 1602, a processor successively transmits, to each slot of a plurality of slots on a wearable device, a command to enable a respective module located in each slot.

In operation 1604, the processor determines, based on an acknowledgment received from a module control circuit of a first module when the command is transmitted to a first slot, that the first module is enabled and located in the first slot.

In operation 1606, the processor successively transmits, based on the determining that the first module is enabled and located in the first slot, a plurality of detector address identifiers, each detector address identifier of the plurality of detector address identifiers transmitted while the module control circuit places a different detector of a plurality of detectors of the first module into an enumeration mode to be assigned each detector address identifier.

An exemplary optical measurement system described herein includes a processor, a wearable device comprising a plurality of slots, each slot configured to house a different module, a first module, a second module, etc. The first module includes a plurality of detectors and a module control circuit configured to communicate with the plurality of detectors and with the processor. The processor is configured to successively transmit, to each slot of the plurality of slots, a command to enable a respective module located in each slot. The processor is further configured to determine, based on an acknowledgment received from the module control circuit when the command is transmitted to a first slot, that the first module is enabled and located in the first slot. The processor is further configured to successively transmit, based on the determining that the first module is enabled and located in the first slot, a plurality of detector address identifiers. The module control circuit is configured to, while the plurality of detector address identifiers are being successively transmitted, successively place the plurality of detectors into an enumeration mode in which each detector of the plurality of detectors is assigned a different detector address identifier of the plurality of detector address identifiers.

An exemplary system described herein includes a memory storing instructions a processor communicatively coupled to the memory. The processor is configured to execute the instructions to successively transmit, to each slot of a plurality of slots on a wearable device, a command to enable a respective module located in each slot. The processor is further configured to execute the instructions to determine, based on an acknowledgment received from a module control circuit of a first module when the command is transmitted to a first slot, that the first module is enabled and located in the first slot. The processor is further configured to execute the instructions to successively transmit, based on the determining that the first module is enabled and located in the first slot, a plurality of detector address identifiers, each detector address identifier of the plurality of detector address identifiers transmitted while the module control circuit places a different detector of a plurality of detectors of the first module into an enumeration mode to be assigned each detector address identifier.

An exemplary method described herein includes successively transmitting, by a processor to each slot of a plurality of slots on a wearable device, a command to enable a respective module located in each slot. The method further includes determining, by the processor, based on an acknowledgment received from a module control circuit of a first module when the command is transmitted to a first slot, that the first module is enabled and located in the first slot. The method further includes successively transmitting, by the processor, based on the determining that the first module is enabled and located in the first slot, a plurality of detector address identifiers, each detector address identifier of the plurality of detector address identifiers transmitted while the module control circuit places a different detector of a plurality of detectors of the first module into an enumeration mode to be assigned each detector address identifier.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An optical measurement system comprising:
    a processor;
    a wearable device comprising a plurality of slots, each slot configured to house a different module; and
    a first module comprising:
       a plurality of detectors, and
       a module control circuit configured to communicate with the plurality of detectors and with the processor;
    wherein the processor is configured to:
       successively transmit, to each slot of the plurality of slots, a command to enable a respective module located in each slot,
       determine, based on an acknowledgment received from the module control circuit when the command is transmitted to a first slot, that the first module is enabled and located in the first slot, and
       successively transmit, based on the determining that the first module is enabled and located in the first slot, a plurality of detector address identifiers; and
    wherein, while the plurality of detector address identifiers are being successively transmitted, the module control circuit is configured to successively place the plurality of detectors into an enumeration mode in which each detector of the plurality of detectors is assigned a different detector address identifier of the plurality of detector address identifiers.

2. The optical measurement system of claim 1, wherein the processor is further configured to determine, based on an absence of an acknowledgment received when the command is transmitted to a second slot of the plurality of slots, that no module is located in the second slot.

3. The optical measurement system of claim 1, wherein each slot of the plurality of slots has a different predetermined slot address.

4. The optical measurement system of claim 3, wherein the plurality of detector address identifiers are based on the different predetermined slot addresses.

5. The optical measurement system of claim 1, wherein each detector address identifier of the plurality of detector address identifiers is broadcast to any detector in the enumeration mode.

6. The optical measurement system of claim 5, wherein the successively placing the plurality of detectors into the enumeration mode in which each detector of the plurality of detectors is assigned to the different detector address identifier comprises enabling each detector for a time period that corresponds to when a different detector address identifier of the plurality of detector address identifiers is being broadcast such that each detector receives and stores the different detector address identifier.

7. The optical measurement system of claim 1, wherein the module control circuit comprises an input/output (I/O) expander configured to communicate with the processor via a first shared communication bus.

8. The optical measurement system of claim 7, wherein the command to enable the respective module located in each slot comprises a scan chain signal configured to enable the I/O expander.

9. The optical measurement system of claim 7, wherein the plurality of detectors are configured to communicate with the processor via a second shared communication bus.

10. The optical measurement system of claim 1, wherein the processor is further configured to transmit additional setup information to each detector in the enumeration mode.

11. The optical measurement system of claim 1, wherein each slot of the plurality of slots is configured to house the module in a predetermined orientation.

12. The optical measurement system of claim 1, wherein:
    the processor is further configured to receive, from the module control circuit, a module identifier of the first module; and
    the plurality of detector address identifiers are based on the module identifier.

13. The optical measurement system of claim 1, where each detector of the plurality of detectors comprises a photodetector configured to detect a photon from a light pulse directed toward a target of a body of a user of the wearable device.

14. The optical measurement system of claim 13, wherein the first module further comprises a light source configured to generate the light pulse.

15. The optical measurement system of claim 13, wherein each photodetector comprises:
    a single photon avalanche diode (SPAD); and
    a fast gating circuit configured to arm and disarm the SPAD.

16. The optical measurement system of claim 1, wherein the wearable device includes a head-mountable component configured to be worn on a head of a user.

17. The optical measurement system of claim 1, wherein the processor is housed in the wearable device.

18. A system comprising:
a memory storing instructions; and
a processor communicatively coupled to the memory and configured to execute the instructions to:
successively transmit, to each slot of a plurality of slots on a wearable device, a command to enable a respective module located in each slot,
determine, based on an acknowledgment received from a module control circuit of a first module when the command is transmitted to a first slot, that the first module is enabled and located in the first slot, and
successively transmit, based on the determining that the first module is enabled and located in the first slot, a plurality of detector address identifiers, each detector address identifier of the plurality of detector address identifiers transmitted while the module control circuit places a different detector of a plurality of detectors of the first module into an enumeration mode to be assigned each detector address identifier.

19. The system of claim 18, wherein the processor is further configured to determine, based on an absence of an acknowledgment received when the command is transmitted to a second slot of the plurality of slots, that no module is located in the second slot.

20. The system of claim 18, wherein each slot of the plurality of slots has a different predetermined slot address.

21. The system of claim 20, wherein the plurality of detector address identifiers are based on the different predetermined slot addresses.

22. The system of claim 18, wherein each detector address identifier of the plurality of detector address identifiers is broadcast to any detector in the enumeration mode.

23. The system of claim 18, wherein the processor is configured to communicate with an input/output (I/O) expander of the module control circuit via a first shared communication bus.

24. The system of claim 23, wherein the command to enable the respective module located in each slot comprises a scan chain signal configured to enable the I/O expander.

25. The system of claim 23, wherein the processor is configured to communicate with the plurality of detectors via a second shared communication bus.

26. The system of claim 18, wherein the processor is further configured to transmit additional setup information to each detector in the enumeration mode.

27. The system of claim 18, wherein:
the processor is further configured to receive, from the module control circuit, a module identifier of the first module; and
the plurality of detector address identifiers are based on the module identifier.

28. A method comprising:
successively transmitting, by a processor to each slot of a plurality of slots on a wearable device, a command to enable a respective module located in each slot,
determining, by the processor, based on an acknowledgment received from a module control circuit of a first module when the command is transmitted to a first slot, that the first module is enabled and located in the first slot, and
successively transmitting, by the processor, based on the determining that the first module is enabled and located in the first slot, a plurality of detector address identifiers, each detector address identifier of the plurality of detector address identifiers transmitted while the module control circuit places a different detector of a plurality of detectors of the first module into an enumeration mode to be assigned each detector address identifier.

29. The method of claim 28, further comprising determining, by the processor, based on an absence of an acknowledgment received when the command is transmitted to a second slot of the plurality of slots, that no module is located in the second slot.

* * * * *